United States Patent
Bickley et al.

(10) Patent No.: US 8,506,605 B2
(45) Date of Patent: Aug. 13, 2013

(54) METHOD AND APPARATUS FOR SECURING AN OBJECT TO BONE AND/OR FOR STABILIZING BONE

(75) Inventors: Barry T. Bickley, North Andover, MA (US); Aldo M. Zovich, East Hampton, CT (US); Richard E. Zovich, Kensington, CT (US); Paul Glazer, Brookline, MA (US)

(73) Assignee: Simplicity Orthopedics, Inc., North Andover, MA (US)

( * ) Notice: Subject to any disclaimer, the term of this patent is extended or adjusted under 35 U.S.C. 154(b) by 339 days.

(21) Appl. No.: 12/451,827

(22) PCT Filed: Jun. 2, 2008

(86) PCT No.: PCT/US2008/006928
§ 371 (c)(1),
(2), (4) Date: Aug. 27, 2010

(87) PCT Pub. No.: WO2008/150501
PCT Pub. Date: Dec. 11, 2008

(65) Prior Publication Data
US 2010/0324558 A1    Dec. 23, 2010

Related U.S. Application Data

(63) Continuation-in-part of application No. 12/148,845, filed on Apr. 23, 2008, now Pat. No. 7,967,851, and a continuation-in-part of application No. 10/554,379, filed as application No. PCT/US2004/014640 on May 10, 2004, now Pat. No. 8,419,780, said application No. 10/554,379 is a continuation-in-part of application No. 10/246,304, filed on Sep. 18, 2002, now abandoned.

(60) Provisional application No. 60/468,829, filed on May 8, 2003, provisional application No. 60/932,805, filed on Jun. 1, 2007.

(51) Int. Cl.
*A61B 17/80*    (2006.01)

(52) U.S. Cl.
USPC .............................. 606/280; 606/70; 606/71

(58) Field of Classification Search
USPC ...................................... 606/70–71, 280–299
See application file for complete search history.

(56) References Cited

U.S. PATENT DOCUMENTS

| | | |
|---|---|---|
| 1,752,752 A | 4/1930 | Ogden |
| 2,307,179 A | 1/1943 | Whitehead |

(Continued)

FOREIGN PATENT DOCUMENTS

| | | |
|---|---|---|
| CH | 645 168 A5 | 9/1984 |
| DE | 42 01 531 | 7/1993 |

(Continued)

OTHER PUBLICATIONS

Joseph H. Sklar, M.D.; "Technique for Tibial Fixation of ACL Grafts;" Innovasive Devices; 1999.

(Continued)

*Primary Examiner* — Eduardo C Robert
*Assistant Examiner* — Christina Negrellirodriguez
(74) *Attorney, Agent, or Firm* — Pandiscio & Pandiscio

(57) ABSTRACT

A surgical system for stabilizing a first bone segment to a second bone segment, the system comprising a plate having a first end and a second end, wherein the first end is configured to be secured to the first bone segment and the second end is configured to be secured to the second bone segment, and further wherein the plate has a structural integrity sufficient to stabilize the first bone segment to the second bone segment. Further embodiments comprise a supplemental plate for stabilizing a third bone segment to the second bone segment.

22 Claims, 53 Drawing Sheets

(56) References Cited

U.S. PATENT DOCUMENTS

| | | |
|---|---|---|
| 2,381,050 A | 8/1945 | Hardinge |
| 3,174,387 A | 3/1965 | Fischer |
| 3,232,163 A | 2/1966 | Croessant |
| 3,473,222 A | 10/1969 | Kester |
| 3,896,504 A | 7/1975 | Fischer |
| 4,201,531 A | 5/1980 | Schurman |
| 4,276,806 A | 7/1981 | Morel |
| 4,312,612 A | 1/1982 | Thompson |
| 4,388,921 A | 6/1983 | Sutter et al. |
| 4,484,570 A | 11/1984 | Sutter et al. |
| 4,553,273 A | 11/1985 | Wu |
| 4,601,625 A | 7/1986 | Ernst et al. |
| 4,611,581 A | 9/1986 | Steffee |
| 4,716,893 A | 1/1988 | Fischer et al. |
| 5,084,050 A | 1/1992 | Draenert |
| 5,224,805 A | 7/1993 | Moretti et al. |
| 5,324,292 A | 6/1994 | Meyers |
| 5,356,435 A | 10/1994 | Thein |
| 5,375,954 A | 12/1994 | Eguchi |
| 5,601,558 A | 2/1997 | Torrie et al. |
| 5,713,904 A | 2/1998 | Errico et al. |
| 5,716,359 A | 2/1998 | Ojima et al. |
| 5,720,753 A | 2/1998 | Sander et al. |
| 5,725,529 A | 3/1998 | Nicholson et al. |
| 5,772,662 A | 6/1998 | Chapman et al. |
| 5,871,485 A | 2/1999 | Rao et al. |
| 5,899,938 A | 5/1999 | Sklar et al. |
| 5,976,141 A | 11/1999 | Haag et al. |
| 6,056,750 A | 5/2000 | Lob |
| 6,206,881 B1 | 3/2001 | Frigg et al. |
| 6,290,701 B1 | 9/2001 | Enayati |
| 6,299,642 B1 | 10/2001 | Chan |
| 6,355,044 B1 | 3/2002 | Hair |
| 6,623,486 B1 | 9/2003 | Weaver et al. |
| 7,090,676 B2 | 8/2006 | Huebner et al. |
| 2001/0053913 A1 | 12/2001 | Freedland |
| 2003/0065391 A1 | 4/2003 | Re et al. |
| 2003/0074075 A1 | 4/2003 | Thomas, Jr. et al. |
| 2003/0171753 A1 | 9/2003 | Collins et al. |
| 2003/0176863 A1 | 9/2003 | Ueyama et al. |
| 2004/0162558 A1 | 8/2004 | Hegde et al. |
| 2004/0176767 A1 | 9/2004 | Bickley |
| 2005/0177161 A1 | 8/2005 | Baynham et al. |
| 2005/0216009 A1* | 9/2005 | Michelson ............... 606/69 |
| 2006/0052787 A1 | 3/2006 | Re et al. |
| 2006/0074421 A1 | 4/2006 | Bickley et al. |
| 2006/0173455 A1 | 8/2006 | Matthys |
| 2006/0184170 A1 | 8/2006 | Kapitan et al. |
| 2008/0004626 A1 | 1/2008 | Glazer et al. |
| 2008/0183220 A1 | 7/2008 | Glazer et al. |

FOREIGN PATENT DOCUMENTS

| | | |
|---|---|---|
| DE | 298 23 395 | 9/1999 |
| EP | 0 089 298 A1 | 9/1983 |
| EP | 0 330 328 A1 | 8/1989 |
| EP | 0 596 829 A1 | 5/1994 |
| EP | 0 610 575 A2 | 8/1994 |
| EP | 1 018 321 A2 | 7/2000 |
| EP | 1 018 321 A3 | 10/2001 |
| GB | 89 08 858.1 | 1/1990 |
| GB | 2 266 246 A | 10/1993 |
| GB | 2 307 179 | 5/1997 |
| WO | WO-9835635 A1 | 8/1998 |
| WO | WO-98/48738 A1 | 11/1998 |
| WO | WO-02/085182 A2 | 10/2002 |
| WO | WO-03/047440 A2 | 6/2003 |
| WO | WO-2004/006792 A1 | 1/2004 |

OTHER PUBLICATIONS

Regis W. Haid et al.; "The Cervical Spine Study Group anterior cervical plate nomenclature"; Neurosurg. Focus; Jan. 2002; pp. 1-6; vol. 12.

Scandius Biomedical; "TriTis Tibial Fixation System and Implant" Brochure from Scandius BioMedical, Inc. website http://www.scandius.comldocuments/TriTisSSheetPlum3.pdf; Jan. 1, 2006.

PCT Search Report and Written Opinion of the ISA for PCT/US2006/000932 dated May 8, 2006.

Cook et al.; "Biomechanical Evaluation and Preliminary Clinical Experience with an Expansive Pedicle Screw Design;" Journal of Spinal Disorders; Jun. 13, 2000; pp. 230-236; vol. 13, No. 3.

Glatzmaier et al.; "Biodegradable Implants for Orthodontic Anchorage. A Preliminary Biomechanical Study;" European Journal of Orthodontics; 1996; pp. 465-469; vol. 18, No. 5.

Gualtieri et al.; "Biological and Mechanical Characteristics of the Interface Between a New Swelling Anchor and Bone;" Journal of Orthopaedic Research; pp. 494-499; vol. 18; The Journal of Bone and Joint Surgery, Inc.

McKoy et al.; "An Expandable Anchor for Fixation in Osteoporotic Bone;" Journal of Orthopaedic Research; Jun. 15, 1998, pp. 545-547; vol. 19.

Polly et al.; "Revision Pedicle Screws;" SPINE; 1998; pp. 1374-1379; vol. 23, No. 12; Lippincott-Raven Publishers.

Sklar; "Intrafix Technique for Tibial Fixation of ACL Grafts;" Innovasive Devices, Inc. P/N 900506, Rev. A; Aug. 2000; 5 Sheets.

PCT Search Report and Written Opinion of the ISA for PCT/US2004/014640 dated Nov. 14, 2004.

Patent Search Report; Smith & Nephew Corporate Patents & Trade Marks Department; Search No. S1951; Search Title Osteoporotic Screw System; Report No. 2002032; Search Period 1970 to Mar. 26, 2002; two sheets.

* cited by examiner

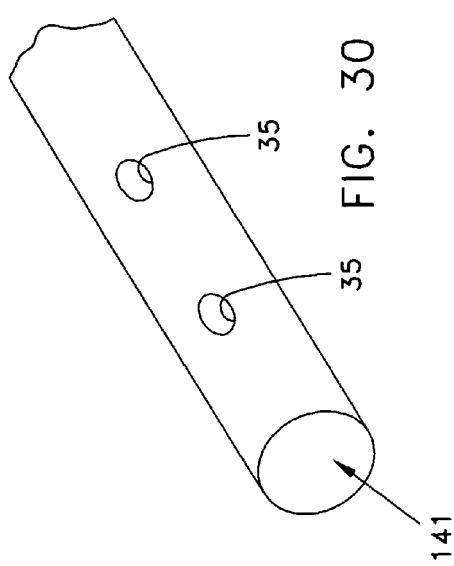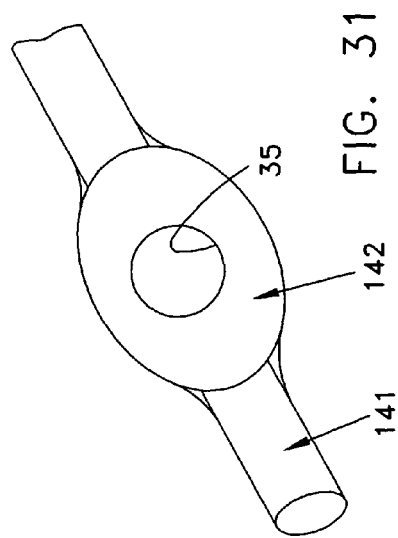

METHOD AND APPARATUS FOR SECURING AN OBJECT TO BONE AND/OR FOR STABILIZING BONE

REFERENCE TO PENDING PRIOR PATENT APPLICATIONS

This patent application:

(1) is a continuation-in-part of pending prior U.S. patent application Ser. No. 10/554,379, filed Oct. 25, 2005 by Barry T. Bickley et al. for FIXATION AUGMENTATION DEVICE AND RELATED TECHNIQUES, which:
 (a) claims benefit of International (PCT) Patent Application No. PCT/US04/14640, filed May 10, 2004 for FIXATION AUGMENTATION DEVICE AND RELATED TECHNIQUES, which itself claims benefit of U.S. Provisional Patent Application Ser. No. 60/468,829, filed May 8, 2003 for FIXATION AUGMENTATION DEVICE; and
 (b) is a continuation-in-part of U.S. Non-Provisional patent application Ser. No. 10/246,304, filed Sep. 18, 2002 for FIXATION AUGMENTATION DEVICE AND RELATED TECHNIQUES;

(2) is a continuation-in-part of pending prior U.S. patent application Ser. No. 12/148,845, filed Apr. 23, 2008 by Barry T. Bickley et al. for METHOD AND APPARATUS FOR SECURING AN OBJECT TO BONE; and (3) claims benefit of prior U.S. Provisional Patent Application Ser. No. 60/932,805, filed Jun. 1, 2007 by Barry T. Bickley et al. for METHOD AND APPARATUS FOR STABILIZING BONE.

The six above-identified patent applications are hereby incorporated herein by reference.

FIELD OF THE INVENTION

This invention relates to surgical methods and apparatus in general, and more particularly to surgical methods and apparatus for securing an object to bone and/or for stabilizing bone.

BACKGROUND OF THE INVENTION

In many situations an object may need to be secured to bone. By way of example but not limitation, where a bone is fractured, it may be desirable to stabilize the bone with a bone plate which extends across the fracture line. By way of further example but not limitation, where two separate bones need to be secured together (e.g., in the case of a spinal fusion), it may be desirable to secure the two bones to one another with a bone plate which extends from one bone to the other. By way of still further example but not limitation, where soft tissue needs to be attached (or re-attached) to bone (e.g., in the case of a ligament repair or reconstruction), it may be desirable to capture the soft tissue to the bone using a fixation plate.

In all of the foregoing situations, as well as many others which are well known to those skilled in the art, a plate or other object needs to be secured to bone. Such attachment is most commonly effected by using a surgical screw which passes through a hole in the plate (or other object) and into the bone.

When using a surgical screw to secure a plate to bone, the plate is first aligned with the bone. Then a hole is drilled into the bone, by passing a drill through a pre-existing hole in the plate and into the bone. Next, the bone hole may be tapped. Then the surgical screw is passed through the hole in the plate and into the hole in the bone, whereby to secure the plate to the bone.

One problem which can arise during the foregoing procedure is that the hole in the bone may become stripped as the screw is inserted into the bone. When this occurs, the screw can no longer obtain adequate purchase in the bone, thereby undermining plate fixation. A screw having inadequate purchase is sometimes referred to as a "spinner". Spinners can occur for many reasons, including (i) inadequate bone quality, (ii) over-tightening of the screw, (iii) an error when drilling the hole in the bone, (iv) an error when tapping the hole in the bone, etc. As noted above, spinners generally result in inadequate fixation.

SUMMARY OF THE INVENTION

The present invention is intended to address the foregoing deficiencies of the prior art, by providing a new and improved method and apparatus for securing an object to bone and/or for stabilizing bone.

More particularly, the present invention provides a new and improved fixation system for securing an object to bone and/or for stabilizing bone.

In one preferred form of the present invention, the new fixation system comprises a plate which is to be secured to bone, and a sleeve and a screw for securing the plate to the bone. The plate comprises an opening which extends through the plate. The plate is placed against the bone and then a drill is used to form a hole in the bone beneath the opening. A sleeve is passed through the opening and into the hole in the bone. The sleeve and plate are formed so that the sleeve (and the recipient bone hole) can be disposed at any one of a variety of angles relative to the plate. A screw is then passed through the sleeve, radially expanding the sleeve so that the sleeve is simultaneously secured to both the bone and the plate.

In another preferred form of the present invention, the new fixation system is intended to stabilize bone in general, and vertebral bodies in particular.

In a preferred form of the present invention, there is provided a novel anterior cervical plate (ACP) system which comprises a novel ACP which is to be attached to two adjacent cervical bodies, and attachment apparatus for attaching the ACP to the two cervical bodies. Preferably, the attachment apparatus comprise a screw and, in one preferred form of the invention, the attachment apparatus comprise a sleeve and screw combination, where the sleeve acts as an interface between (i) the bone and the screw, and (ii) the ACP and the screw, with the sleeve enhancing fixation. Among other things, the ACP is specifically configured to provide the option of adding future level extensions.

In another form of the present invention, there is provided a surgical system for stabilizing a first bone segment to a second bone segment, the system comprising:

a plate having a first end and a second end, wherein the first end is configured to be secured to the first bone segment and the second end is configured to be secured to the second bone segment, and further wherein the plate has a structural integrity sufficient to stabilize the first bone segment to the second bone segment;

the plate comprising a first, generally toroidal body at the first end of the plate, a second generally toroidal body at the second end of the plate, and a bridge connecting the first generally toroidal body to the second generally toroidal body;

the first generally toroidal body comprising at least one opening extending therethrough for receiving attachment apparatus therethrough for securing the first generally toroidal body to the first bone segment, and the second generally toroidal body comprising at least one opening extending therethrough for receiving attachment apparatus therethrough for securing the second generally toroidal body to the second bone segment.

If desired, the surgical system may further comprise:

a supplemental plate for stabilizing a third bone segment to the second bone segment, the supplemental plate having a first end and a second end, wherein the first end is configured to be secured to the second generally toroidal body of the plate and the second end is configured to be secured to the third bone segment, and further wherein the supplemental plate has a structural integrity sufficient to stabilize the third bone segment to the second bone segment;

the supplemental plate comprising a first, generally toroidal body at the first end of the supplemental plate, a second generally toroidal body at the second end of the supplemental plate, and a bridge connecting the first generally toroidal body to the second generally toroidal body;

the first generally toroidal body comprising a cavity extending therethrough for mounting on the second generally toroidal body of the plate so as to secure the supplemental plate to the plate, and the second generally toroidal body comprising at least one opening extending therethrough for receiving attachment apparatus therethrough for securing the second generally toroidal body to the third bone segment.

In another form of the present invention, there is provided a method for stabilizing a first bone segment to a second bone segment, the method comprising:

providing a surgical system comprising:
a plate having a first end and a second end, wherein the first end is configured to be secured to the first bone segment and the second end is configured to be secured to the second bone segment, and further wherein the plate has a structural integrity sufficient to stabilize the first bone segment to the second bone segment;
the plate comprising a first, generally toroidal body at the first end of the plate, a second generally toroidal body at the second end of the plate, and a bridge connecting the first generally toroidal body to the second generally toroidal body;
the first generally toroidal body comprising at least one opening extending therethrough for receiving attachment apparatus therethrough for securing the first generally toroidal body to the first bone segment, and the second generally toroidal body comprising at least one opening extending therethrough for receiving attachment apparatus therethrough for securing the second generally toroidal body to the second bone segment; and
securing the first generally toroidal body to the first bone segment and securing the second generally toroidal body to the second bone segment.

BRIEF DESCRIPTION OF THE DRAWINGS

These and other objects and features of the present invention will be more fully disclosed or rendered obvious by the following detailed description of the preferred embodiments of the invention, which is to be read in conjunction with the attached drawings wherein like numbers refer to like parts, and further wherein:

FIG. 30 is a schematic view showing a rod for use with the sleeve/screw construction of the present invention;

FIG. 31 is a schematic view showing another form of rod for use with the sleeve/screw construction of the present invention;

DETAILED DESCRIPTION OF THE PREFERRED EMBODIMENTS

Method and Apparatus for Securing an Object to Bone

Figure 1:
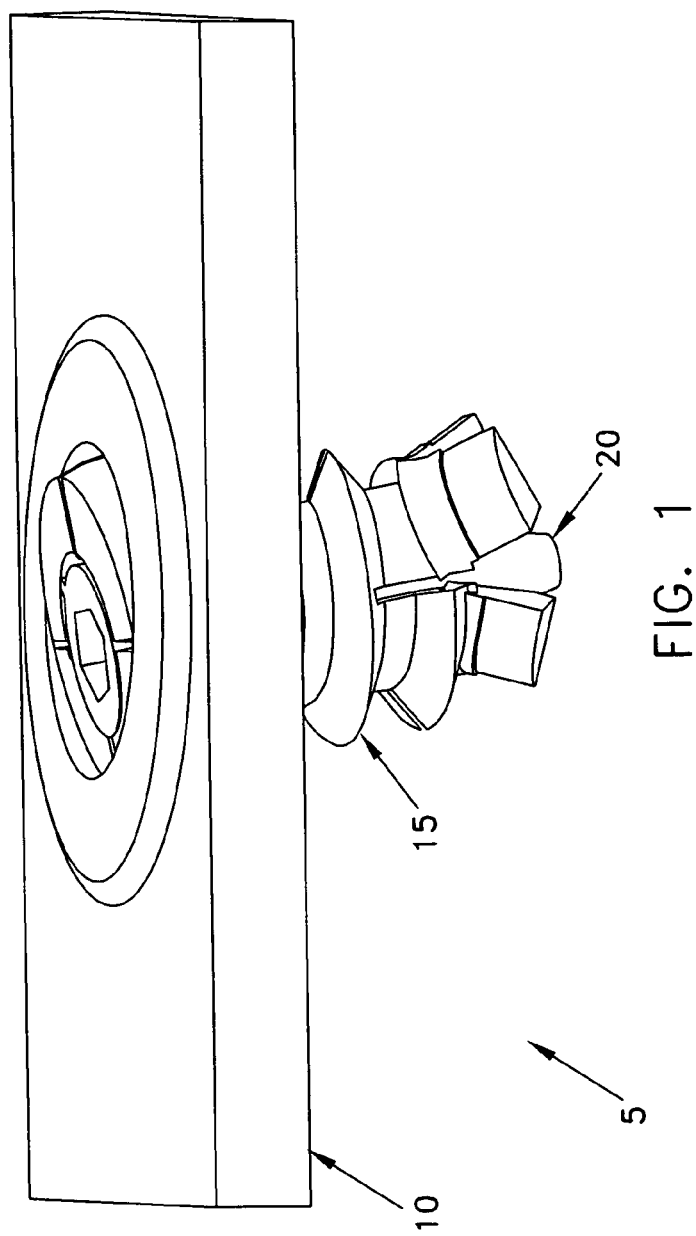
FIG. 1 is a schematic view showing one preferred form of the novel fixation system of the present invention.

Looking first at FIG. 1, there is shown a novel fixation system 5 which generally comprises a plate 10 which is to be secured to bone, a sleeve 15 and a screw 20 for securing plate 10 to the bone.

Figure 2:
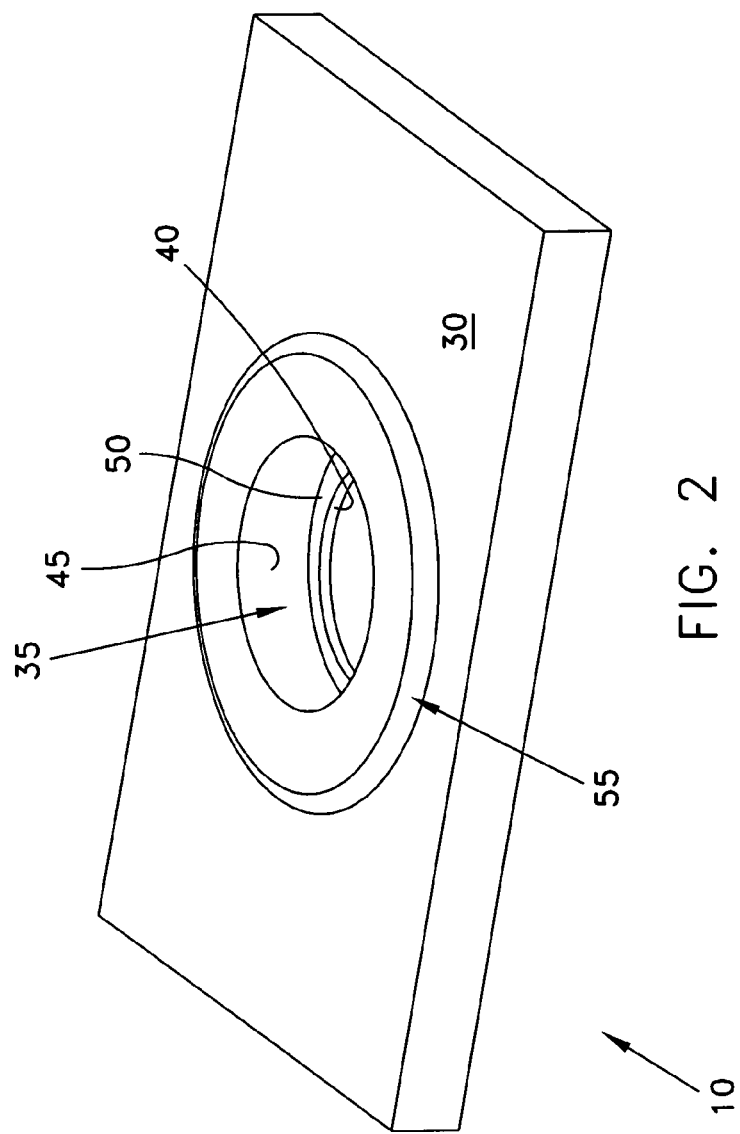
FIGS. 2 and 3 are schematic views showing one preferred form of the plate.
Figure 3:
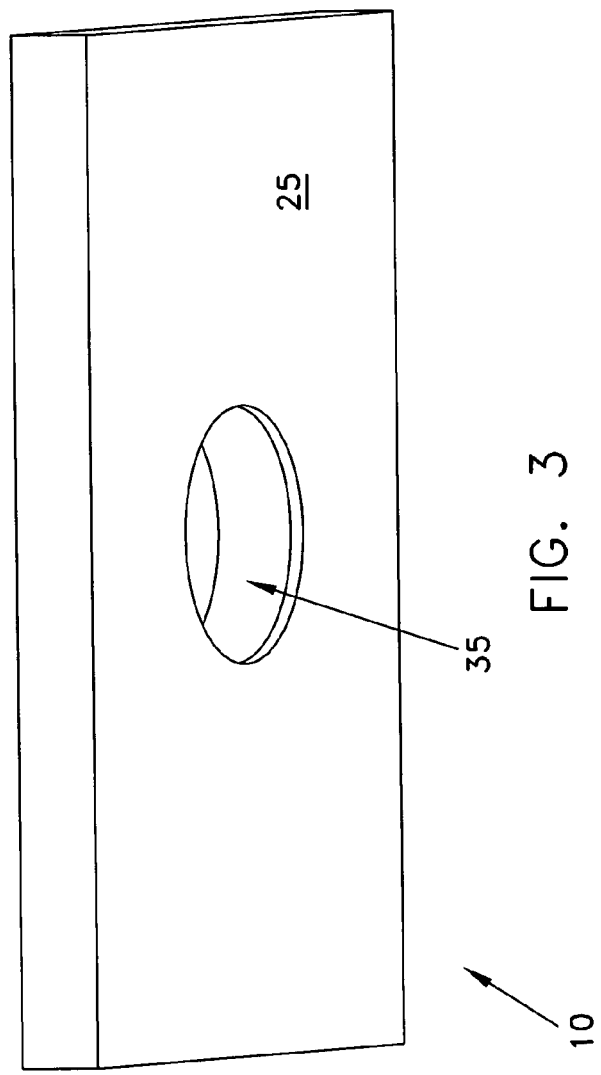

Plate 10 is shown in detail in FIGS. 2 and 3. Plate 10 generally comprises a distal surface 25 (FIG. 3) for positioning against bone, a proximal surface 30 (FIG. 2), and at least one opening 35 formed in the plate. Opening 35 is preferably in the form of a bore-counterbore configuration, i.e., a bore 40 opens on distal surface 25, a counterbore 45 opens on proximal surface 30, and an annular flange 50 is formed at the intersection of bore 40 and counterbore 45. As will hereinafter be discussed in further detail, bore 40 is sized to receive the shank of sleeve 15, and counterbore 45 is sized to receive the head of sleeve 15, with annular flange 50 serving to support the head of sleeve 15 and prevent the head of the sleeve from passing through the plate.

Opening 35 is preferably dimensioned, and one or more of the plate surfaces defining opening 35 are preferably appropriately radiused, and counterpart portions of sleeve 15 are preferably appropriately radiused, in order to permit sleeve 15 to extend through plate 10 at a range of different angles as will hereinafter be discussed in further detail. See, for example, FIG. 1, where sleeve 15 is shown extending through plate 10 at an acute angle.

A raised rim 55 is preferably formed on proximal surface 30 adjacent to opening 35. Raised rim 55 helps to present a smooth interface between the elements of the system and the surrounding tissue, particularly when sleeve 15 and screw 20 are placed at an acute angle relative to the plane of plate 10 (i.e., at an angle significantly off the perpendicular, such as is shown in FIG. 1). In addition, raised rim 55 also provides an enlarged contact surface for the head of sleeve 15, particularly when sleeve 15 and screw 20 are placed at an acute angle relative to the plane of plate 10 (i.e., an angle significantly off the perpendicular). See, for example, FIG. 1.

Depending on the intended use of plate 10, more than one opening 35 may be provided. By way of example but not limitation, where plate 10 is intended to be used as a fracture fixation plate or as a spinal fusion plate, at least one (and preferably two or more) openings 35 are formed in plate 10 on either side of the bone separation line (e.g., the fracture line, the vertebral body abutment lines, etc.), such that plate 10 can be secured to bone on each side of the bone separation line. By way of further example but not limitation, where plate 10 is intended to be used to secure soft tissue to bone, plate 10 might include only one opening 35.

Figure 4:
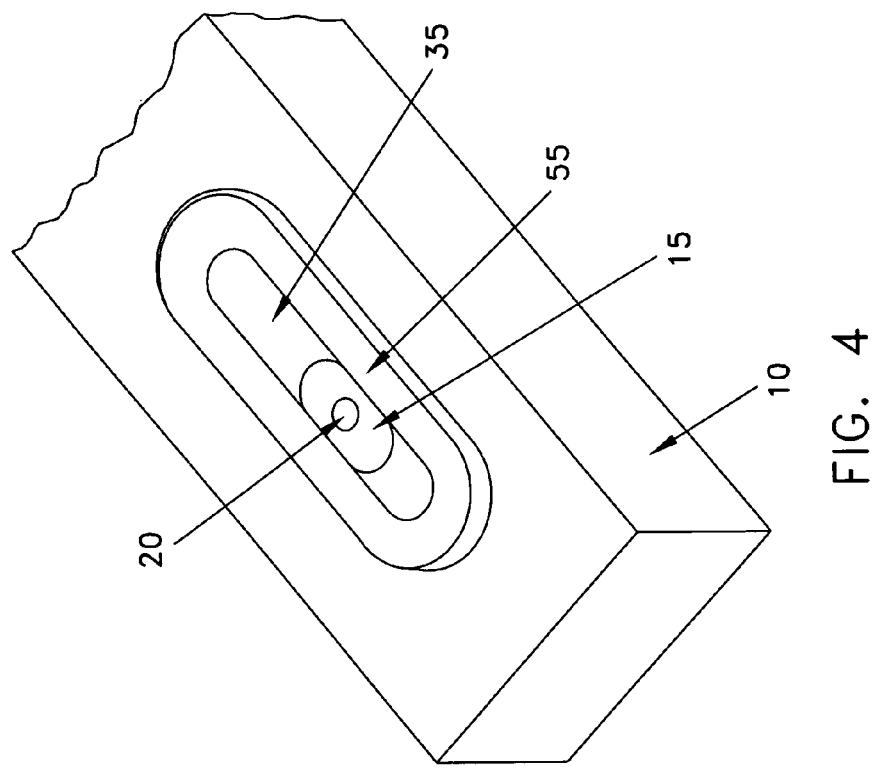
FIG. 4 is a schematic view showing an alternative form of plate and sleeve.
Figure 5:
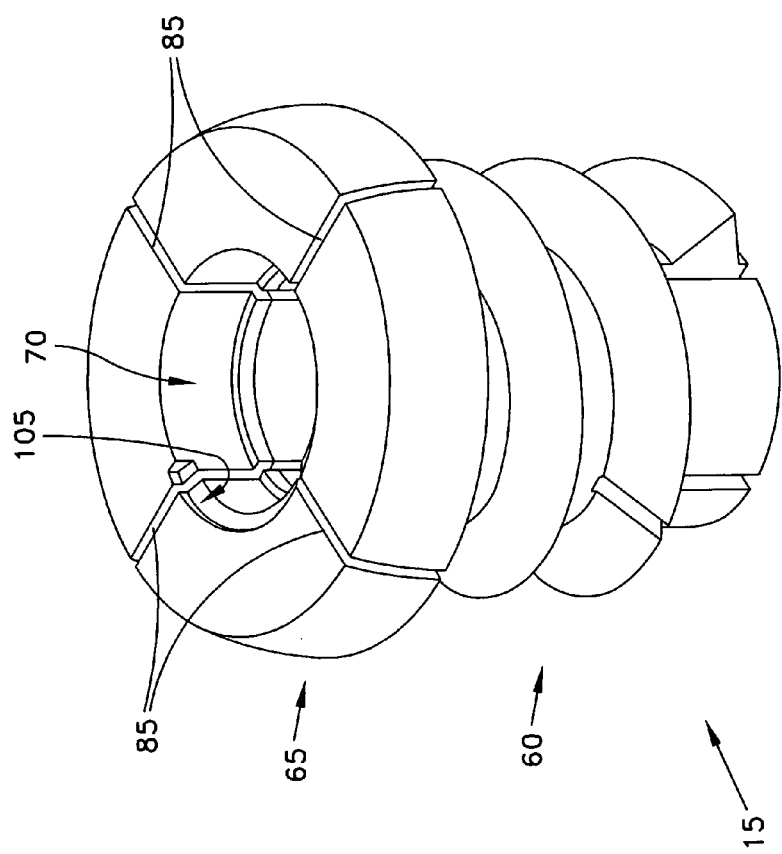
FIGS. 5-10 are schematic views showing one preferred form of the sleeve.
Figure 6:
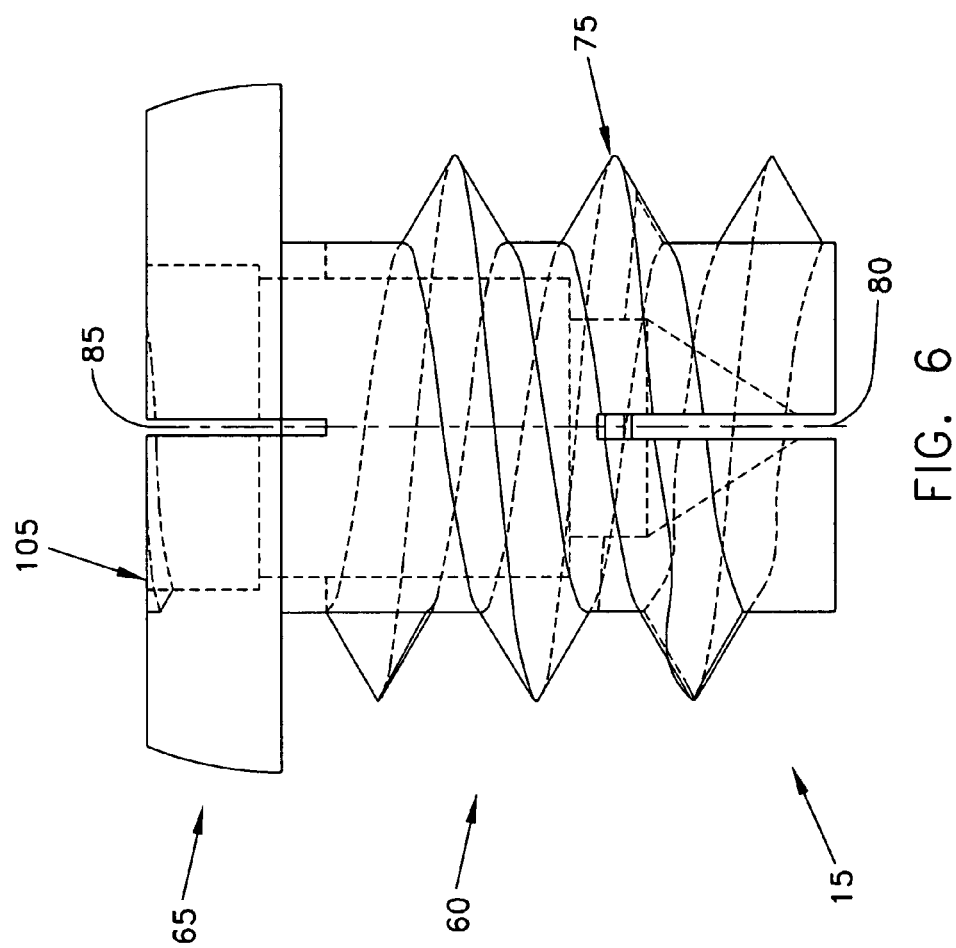
Figure 7:
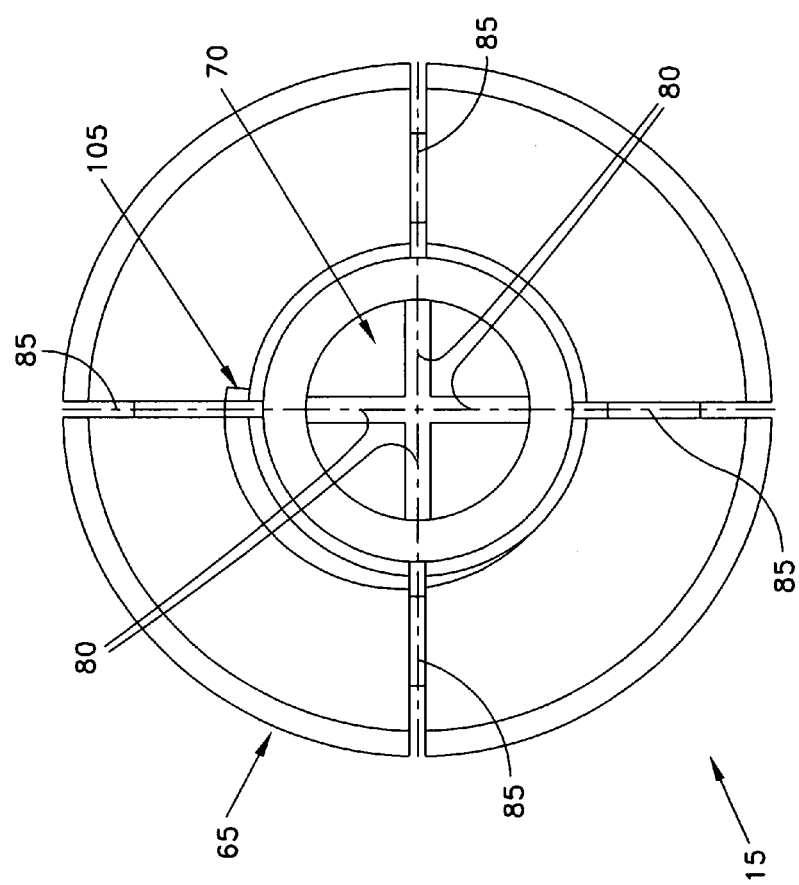
Figure 8:
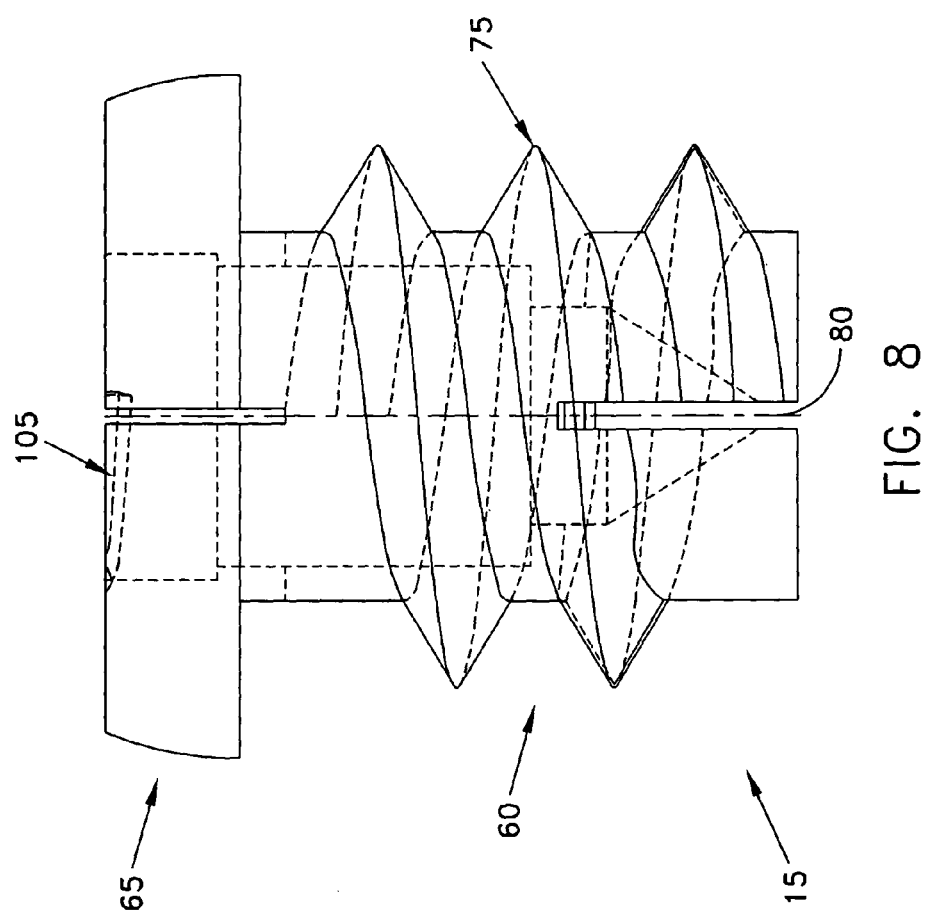
Figure 9:
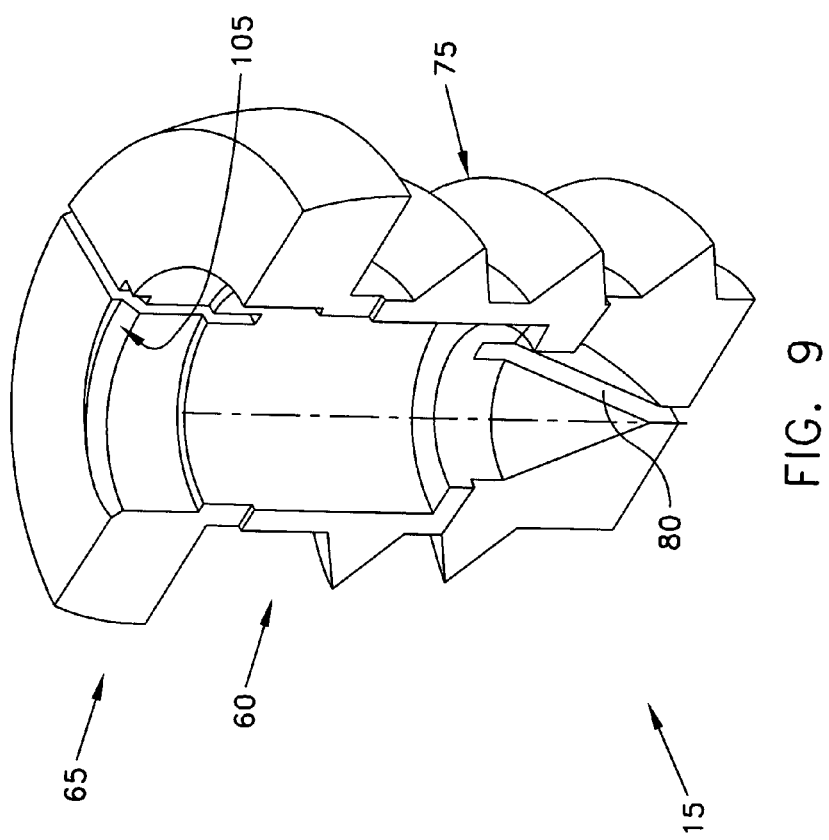
Figure 10:
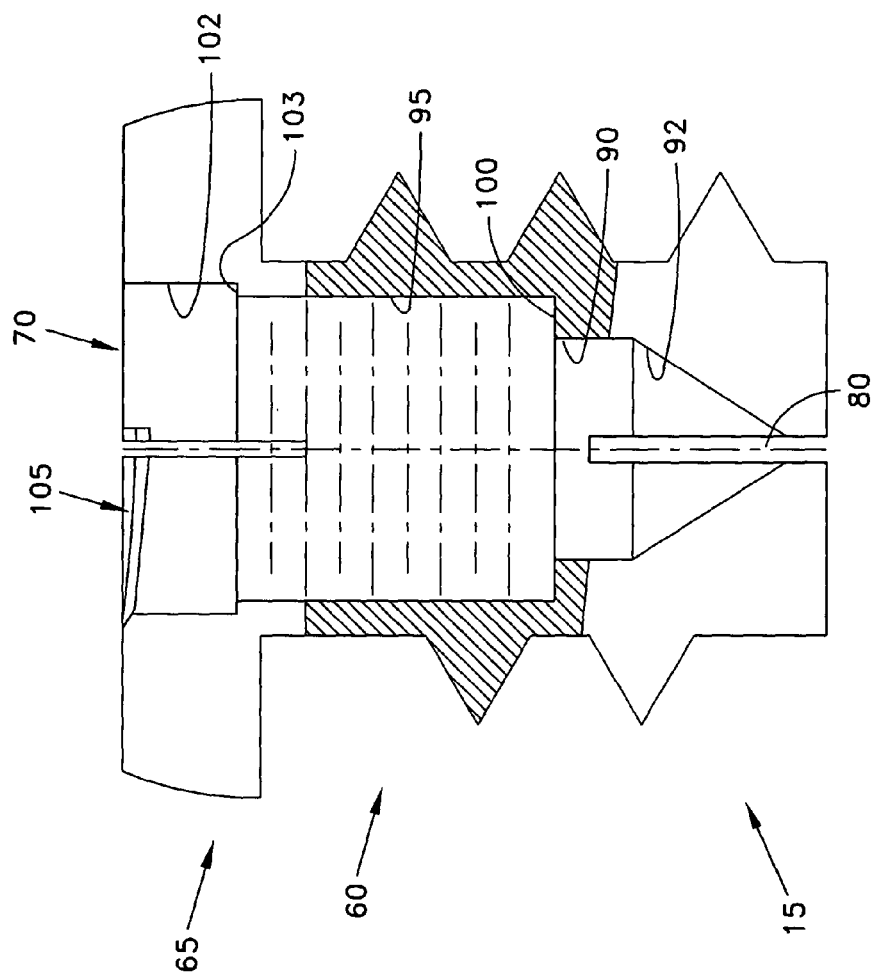
Figure 11:
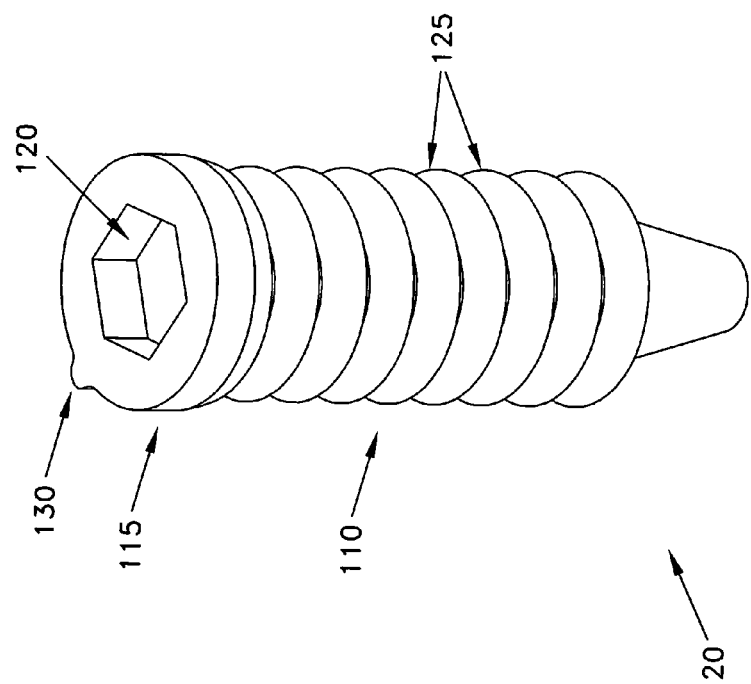
FIGS. 11-14 are schematic views showing one preferred form of the screw.
Figure 12:
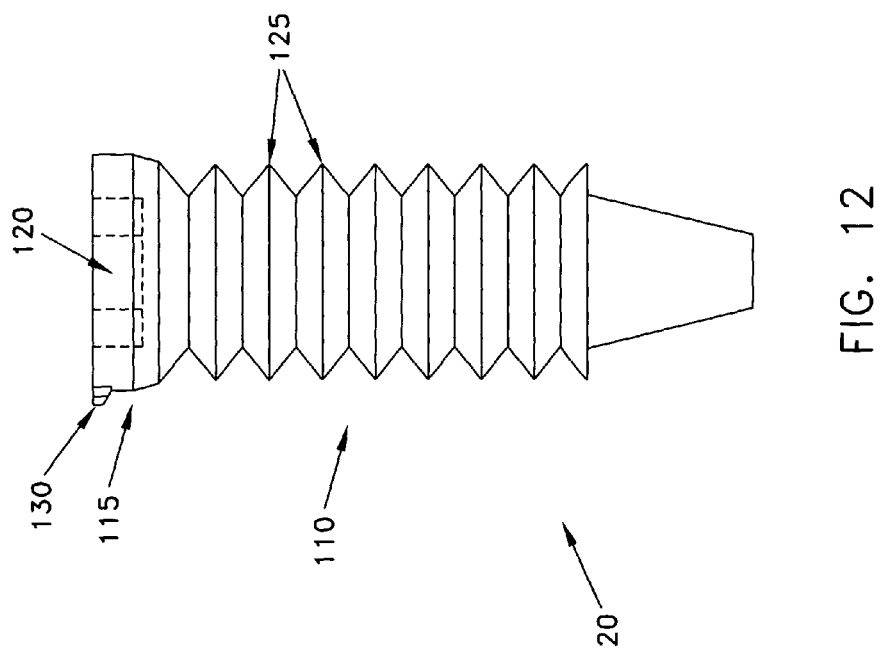
Figure 13:
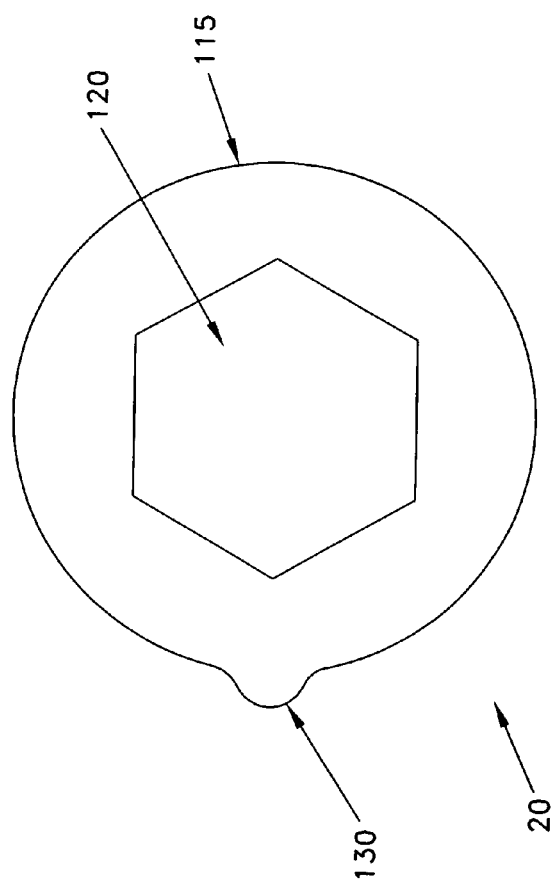
Figure 14:
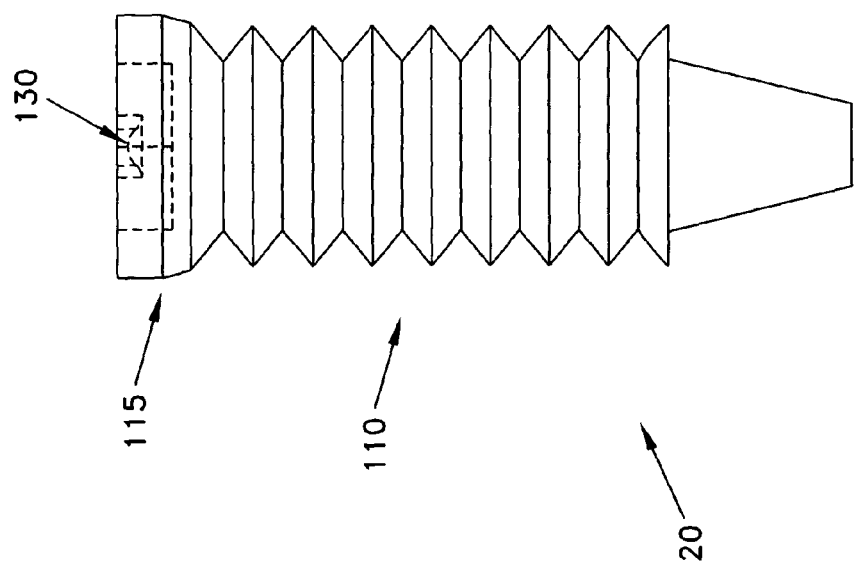

If desired, opening 35 in plate 10 and head 65 of sleeve 15 may be formed with non-circular (e.g., oval) shapes (as seen in top view) so as to provide an anti-rotation contact between the sleeve and the plate. Furthermore, if desired, opening 35 in plate 10 can have a slot-like configuration (as seen in top view), so as to allow a degree of longitudinal freedom when determining where to place sleeve 15 through opening 35 in plate 10. See FIG. 4.

Sleeve 15 is shown in detail in FIGS. 5-10. Sleeve 15 generally comprises a shank 60, a head 65 and an opening 70 extending along the length of sleeve 15.

Shank 60 comprises a screw thread 75 on its outer surface. Screw thread 75 is preferably configured to facilitate the gripping entry of sleeve 15 into bone when the sleeve is turned into bone. Such screw threads may be self-drilling, in which case it may not be necessary to pre-drill a hole in the bone. Furthermore, the threads may be self-tapping, or they may not be self-tapping, in which case it may be necessary to tap a bone hole before inserting the sleeve into that bone hole. Sleeve 15 may be formed with threads having a reverse face so as to aid in backing the sleeve out of the bone, in the event that the same should be desired (e.g., in the case of a revision).

A plurality of slits 80 extend through the side wall of shank 60 at the distal end of shank 60. Slits 80 permit shank 60 to expand radially when screw 20 is disposed in opening 70, as will hereinafter be discussed in further detail.

Head 65 includes a plurality of longitudinally-extending slots 85. Slots 85 permit sleeve 15 to be held against rotation as screw 20 is turned into the sleeve, as will hereinafter be discussed in further detail. Slots 85 also permit head 65 to expand when screw 20 is turned into the sleeve, whereby to facilitate head 65 gripping adjacent portions of plate 10, as will hereinafter be discussed in further detail. Additionally, the head of sleeve 15 can be formed with a beveled edge so that it stands less proud when the sleeve is inserted into plate 10 at an angle which is relatively far off the perpendicular.

Opening 70 comprises a bore-counterbore-counterbore configuration. More particularly, and looking now at FIG. 10, a bore 90, terminating in a tapered portion 92, communicates with distal slits 80. A counterbore 95 communicates with bore 90. An annular flange 100 is formed at the intersection of bore 90 and counterbore 95. Another counterbore 102 communicates with counterbore 95 and opens on the proximal end of sleeve 15. An annular shoulder 103 is formed at the intersection of counterbore 95 and counterbore 102. As will hereinafter be discussed, counterbore 95 is sized to receive the shank of screw 20, and counterbore 102 is sized to receive the head of screw 20, with annular shoulder 103 serving to support the head of screw 20. However, sleeve 15 and screw 20 are sized so that when screw 20 is received in opening 70 of sleeve 15, engagement of the shank of screw 20 with tapered portion 92 of sleeve 15 will radially expand the distal end of sleeve 15 so as to grip the bone. Furthermore, sleeve 15 and screw 20 are also sized so that when the head of screw 20 is seated in counterbore 102, screw 20 will radially expand head 65 of sleeve 15 so as to grip plate 10.

It should be appreciated that (i) the size and shape of the head of screw 20, (ii) the size and shape of counterbore 102, and (iii) the size and shape of slots 85 in the head of sleeve 15, can all be combined so as to "tune" the degree of expansion of head 65 of sleeve 15, whereby to regulate the force with which the sleeve is secured to plate 10.

In addition to the foregoing, and as will hereinafter be discussed in further detail, sleeve 15 is preferably sized so that, when sleeve 15 is deployed in a plate 10 and into a bone, the distal end of shank 60 will extend beyond the cortical bone/cancellous bone interface, so as to provide enhanced stabilization.

Thus, advancing screw 20 into sleeve 15 radially expands both the distal and proximal ends of sleeve 20, such that the sleeve is simultaneously secured to both the bone and the plate, as will hereinafter be discussed in further detail.

Bore 95 is preferably threaded so as to securely receive the shank of screw 20.

A radially-extending detent 105 is preferably formed in the side wall of counterbore 102, in order to receive a counterpart locking finger (see below) of screw 20, whereby to releasably lock screw 20 to sleeve 15, as will hereinafter be discussed in further detail.

Screw 20 is shown in detail in FIGS. 11-14. Screw 20 generally comprises a shank 110, a head 115 and an opening 120 extending longitudinally into screw 20. Shank 110 comprises a thread 125 on its outer surface. As noted above, head 115 includes a radially-extending locking finger 130 for seating in the radially-extending detent 105 formed in sleeve 15, whereby to releasably lock screw 20 to sleeve 15, as will hereinafter be discussed in further detail. Opening 120 has a non-circular cross-section (e.g., hexagonal), in order that screw 20 can be rotatably driven by an appropriate driver. Preferably screw 20 is sized so that when it is seated within sleeve 15, the distal end of the screw projects out of the distal end of the sleeve (see FIG. 1).

Sleeve 15 and screw 20 can be used to secure a plate to bone. By way of example but not limitation, sleeve 15 and screw 20 can be used to secure plate 10 to a fractured bone so as to stabilize that bone. In this circumstance, plate 10 extends across the fracture line, with each end of the plate being secured to the bone using a sleeve/screw construction. Significantly, each sleeve/screw construction can be oriented at a different angle relative to plate 10, so as to better distribute load and/or apply a compressive force.

Figure 15:
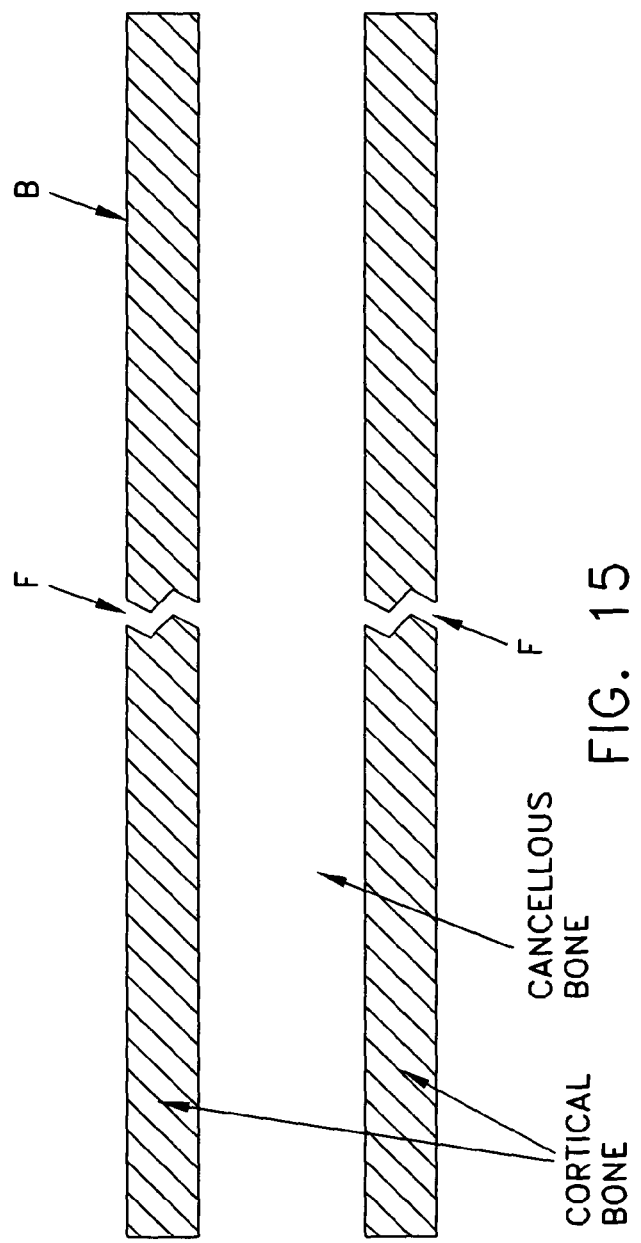
FIGS. 15-20 are schematic views showing the plate being secured to a bone using a plurality of sleeve/screw constructions.
Figure 16:
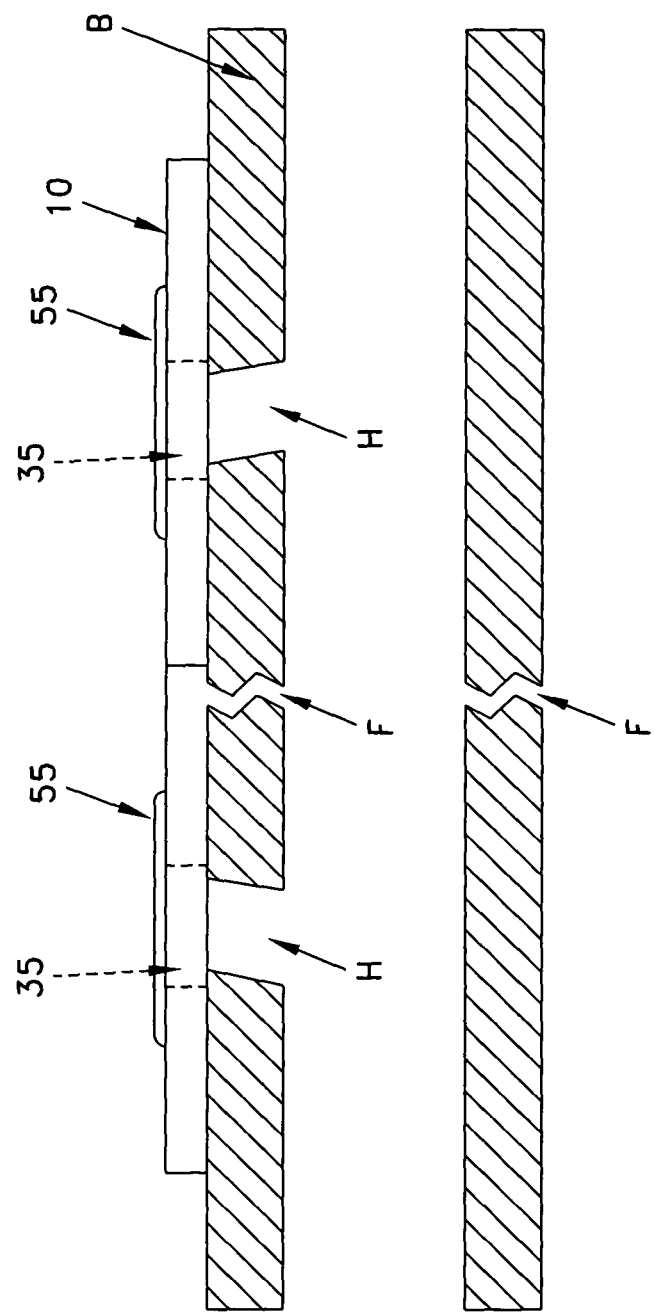

More particularly, and looking now at FIG. 15, there is shown a bone B having a fracture F. In order to stabilize fracture F, a plate may be secured to the bone on either side of fracture F. To this end, and looking now at FIG. 16, plate 10 is positioned against bone B, and then a bone hole H is drilled into the bone beneath each of the openings 35 which are to receive a sleeve/screw construction. This is done by passing a drill through opening 35 in plate 10 and into the bone. Due to the construction of plate 10 and sleeve 15, bone hole H can be set at any one of a number of different orientations relative to plate 10, e.g., bone hole H can extend at an acute angle relative to the plane of plate 10 (see, for example, FIG. 16) or bone hole H can extend at a right angle to the plane of plate 10 (not shown). This construction allows the surgeon to select the most desirable orientation for the bone hole, taking into account factors such as bone quality, force distribution, angle of approach, etc.

Figure 17:
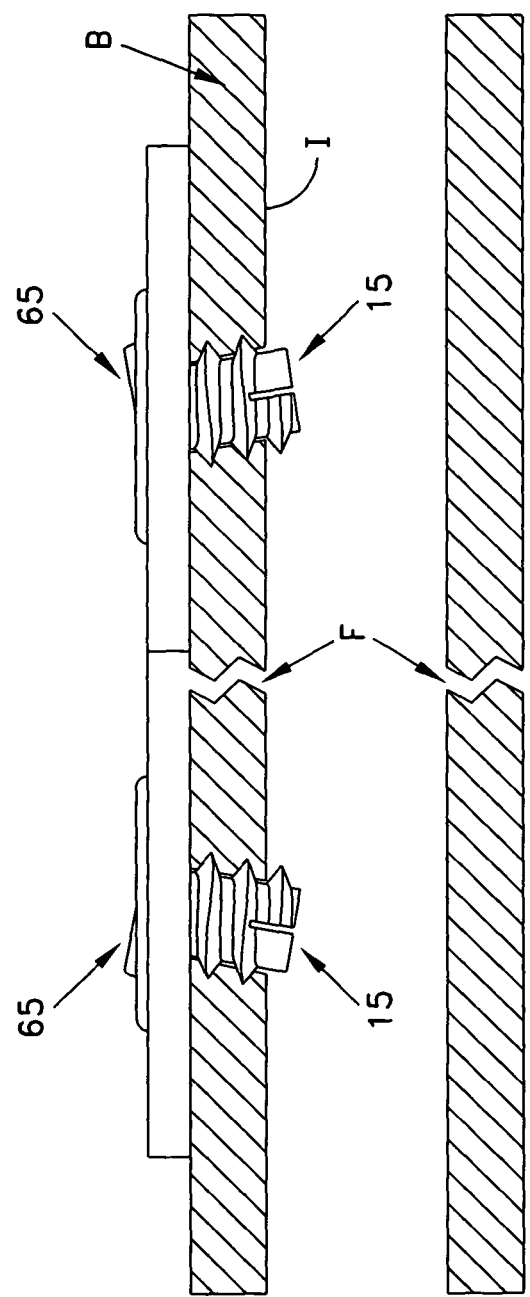
Figure 18:
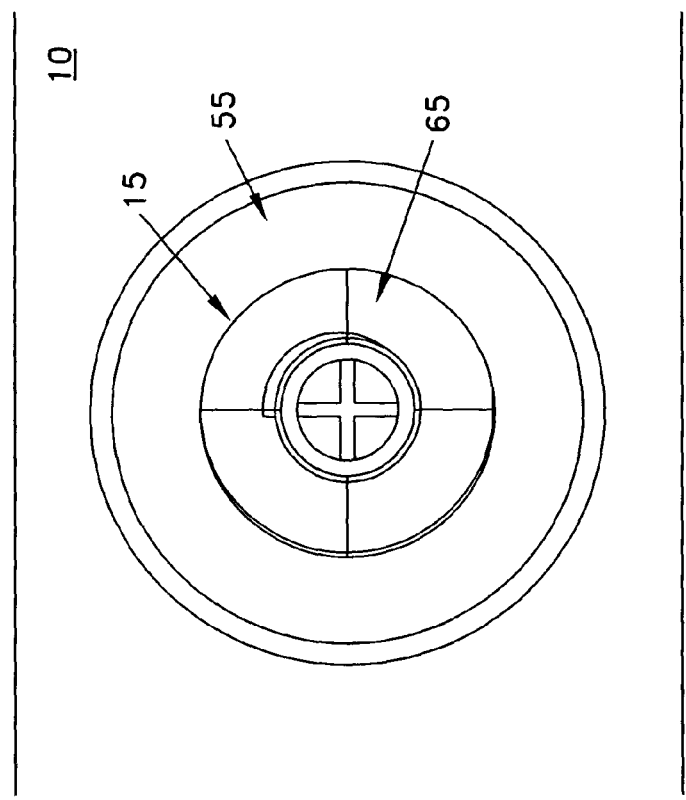

Once bone holes H have been drilled in bone B, sleeves 15 are advanced through plate openings 35 and into bone holes H (FIGS. 17 and 18). This is done by turning sleeve 15 with an appropriate rotational driver. Sleeve 15 is advanced until shank 60 is disposed in bone B and head 65 is seated in plate counterbore 45. At this point, sleeve 15 will serve to provide some degree of attachment of plate 10 to bone B, by virtue of the engagement of screw threads 75 with bone B and head 65 with counterbore 45.

As noted above, sleeve 15 is preferably sized so that, when sleeve 15 is deployed in a plate 10 and into bone B (FIG. 17), the distal end of shank 60 extends beyond the cortical bone/cancellous bone interface I, so as to provide enhanced stabilization, as will hereinafter be discussed in further detail.

Figure 19:
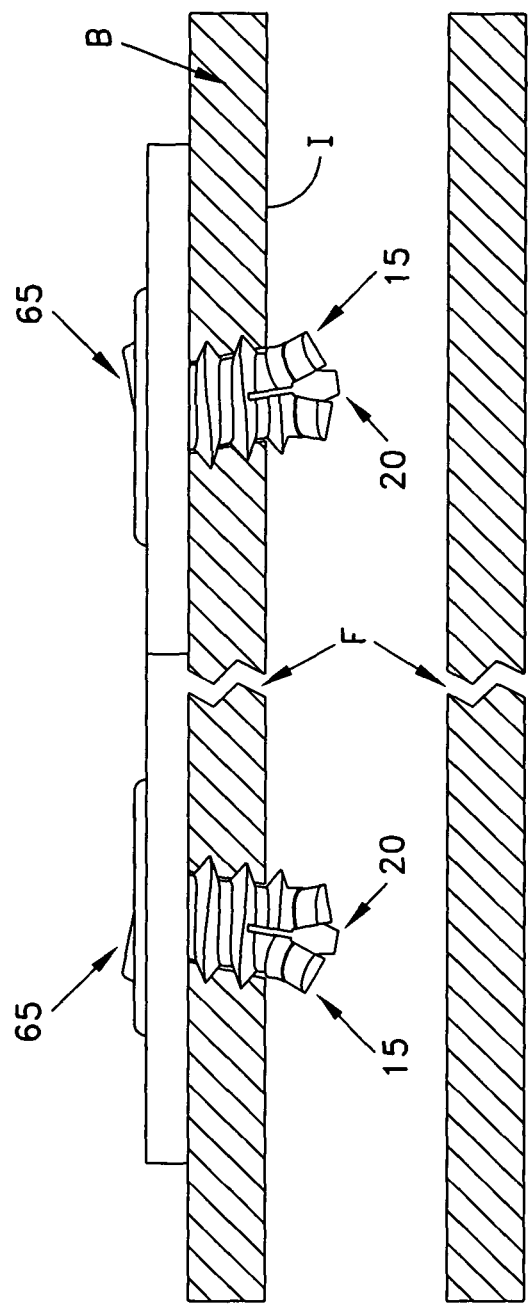
Figure 20:
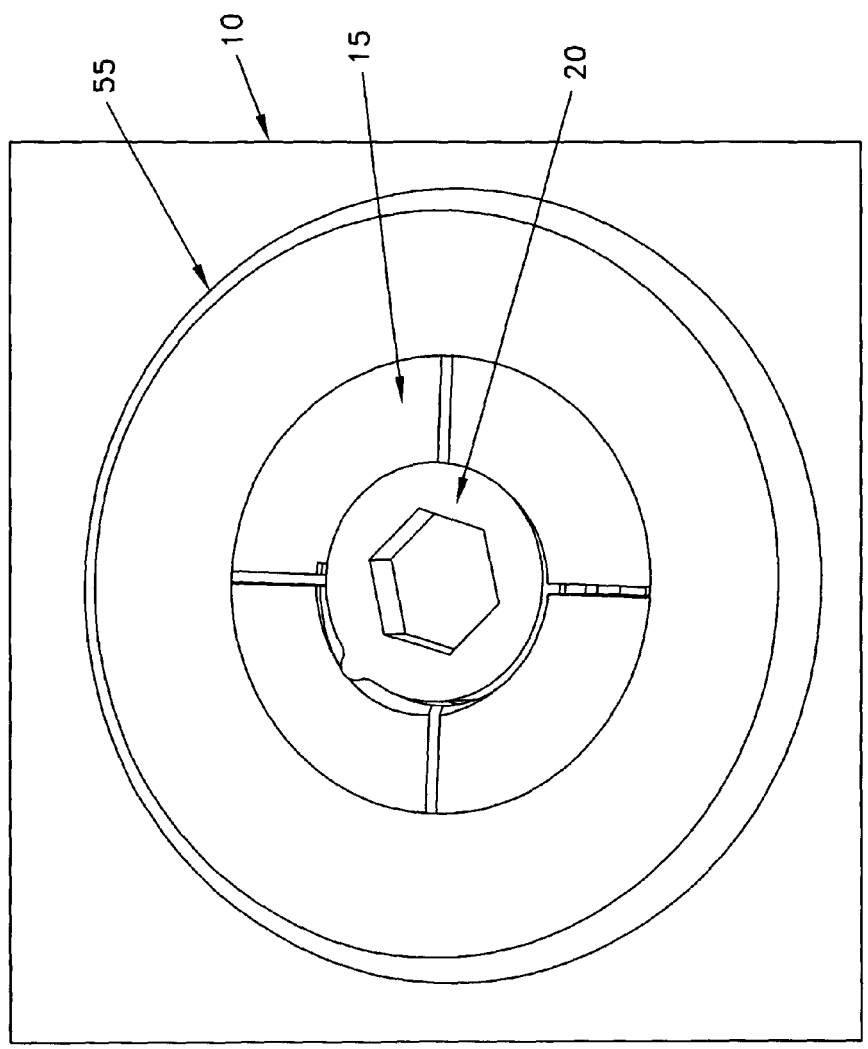
Figure 21:
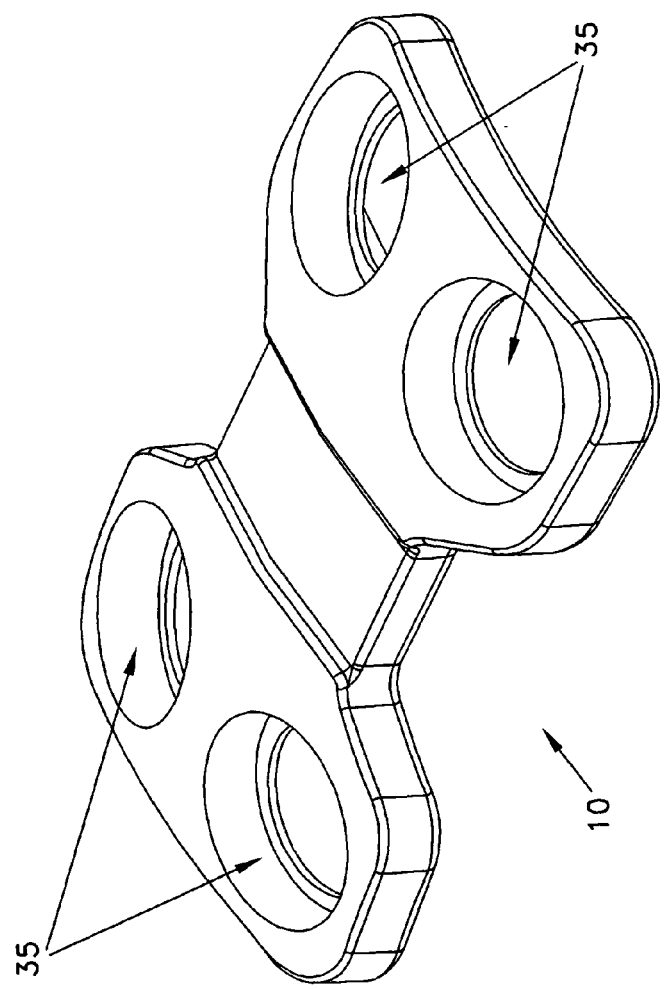
FIGS. 21-25 are schematic views showing another preferred form of the plate.
Figure 22:
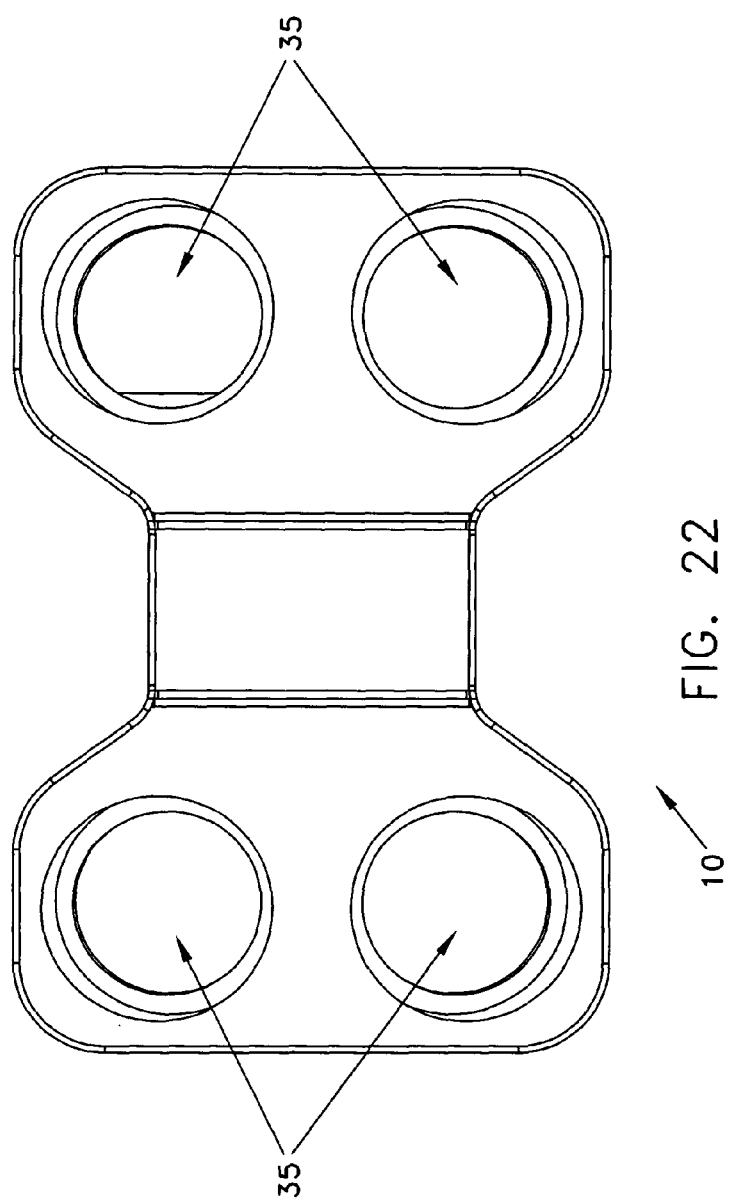
Figure 23:
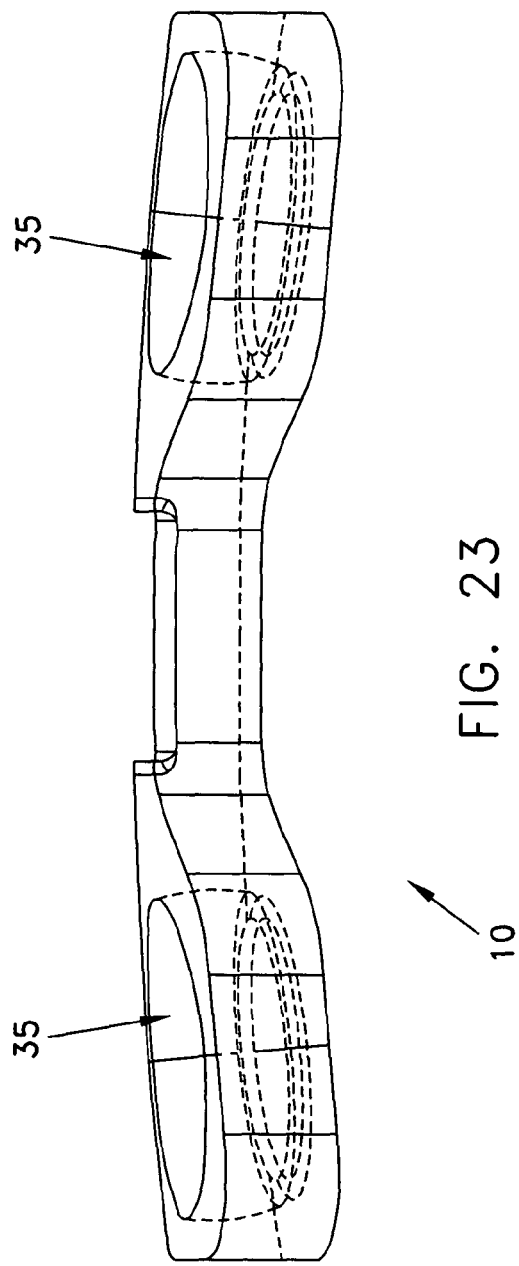
Figure 24:
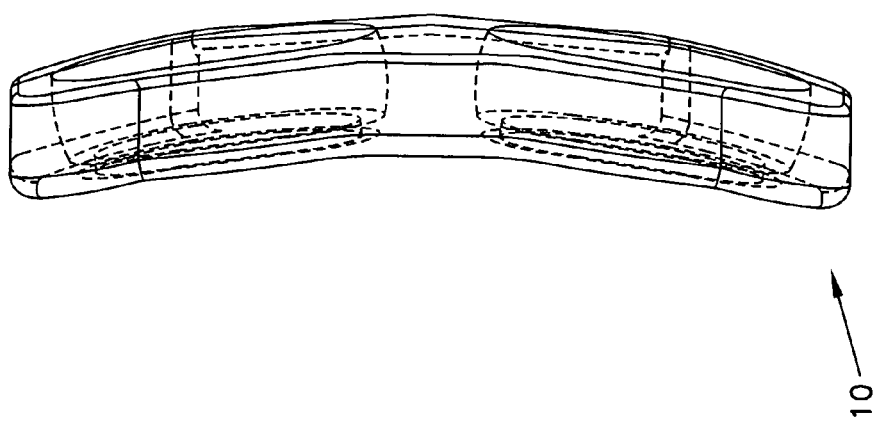
Figure 25:
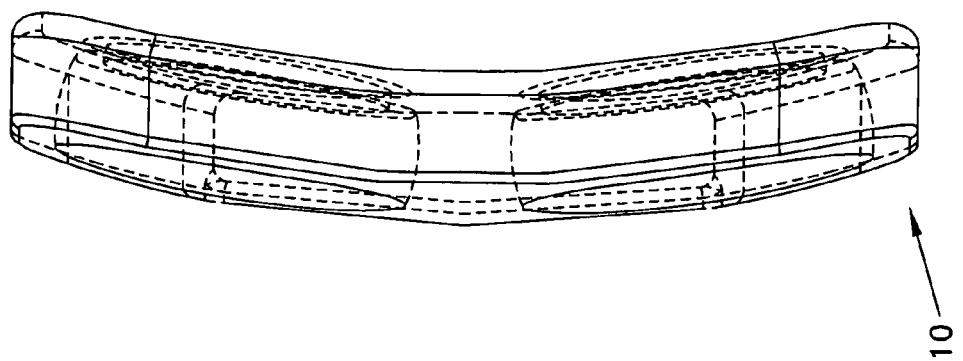

Next, screw 20 is advanced down opening 70 in sleeve 15 (FIGS. 19 and 20). As this occurs, sleeve 15 can be held against rotation using sleeve slots 85. The advancing screw 20 causes sleeve 15 to be radially expanded, so that the sleeve is simultaneously secured to both bone B and to plate 10. More particularly, the distal end of shank 60 of sleeve 15 is expanded so that the sleeve engages the cancellous portion of bone B, the proximal end of shank 60 of sleeve 15 engages the cortical portion of bone B, and head 65 of sleeve 15 engages plate 10. Significantly, sleeve 15 is sized so that the distal end of the sleeve mushrooms open beyond the cancellous bone/cortical bone interface I, making a tight securement between plate 10 and bone B.

Screw 20 is advanced until locking finger 130 seats in sleeve detent 105, thereby releasably locking the screw in position relative to the sleeve. Engagement of locking finger 130 in sleeve detent 105 also serves as an indicator, with tactile feedback, that the screw has been advanced to the proper extent (and not overtightened) relative to the sleeve.

Significantly, inasmuch as sleeve 15 opens laterally and presents a substantially larger profile than screw 20 alone, the disposition of the combination of sleeve and screw in the plate and the bone provides much better contact with the plate and the bone, thereby enhancing securement and shear resistance. This is particularly true since the distal end of sleeve 15 opens just beyond the cortical bone/cancellous bone interface I, so that plate 10 is secured to bone B under tension. In addition, since screw 20 is being advanced into sleeve 15 and not directly into the bone, there is little likelihood that the screw will lose its purchase and become a spinner. Furthermore, in the unlikely event that the screw should become a spinner, the situation can be easily rectified by removing screw 20 from sleeve 15 and removing sleeve 15 from the bone and plate 10. This leaves the host bone in condition for the procedure to be repeated with a new sleeve and/or a new screw, reusing the same bone hole.

Additional Constructions

It is possible to modify the constructions described above without departing from the scope of the present invention.

By way of example but not limitation, plate 10 might be formed with a non-rectangular and/or curved configuration, so as to seat more securely against a curved bone surface. See, for example, FIGS. 21-25, which show one such construction for plate 10.

Figure 26:
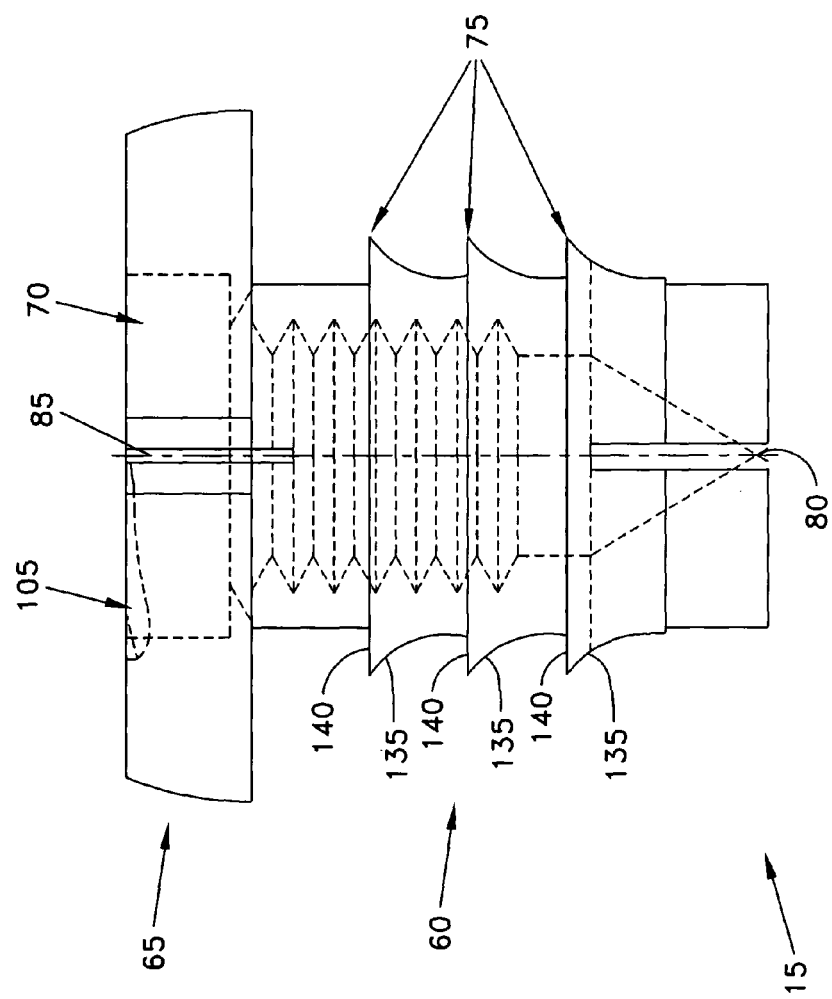
FIGS. 26-28 are schematic views showing another preferred form of the sleeve.
Figure 27:
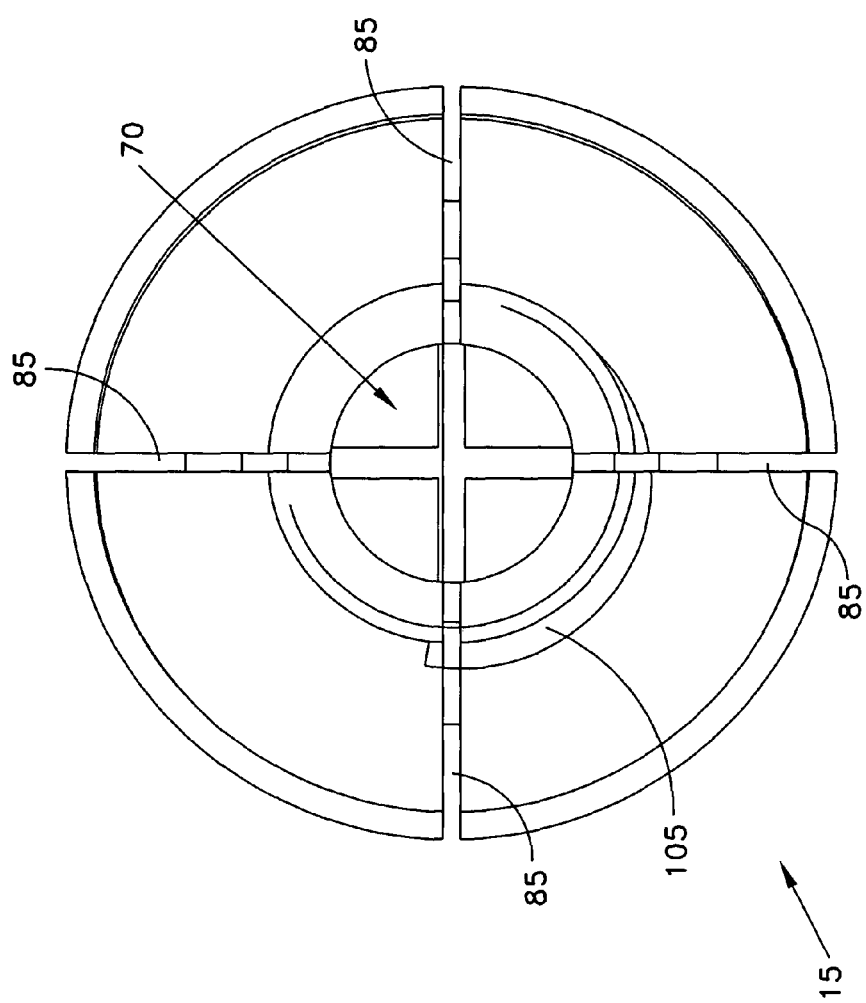
Figure 28:
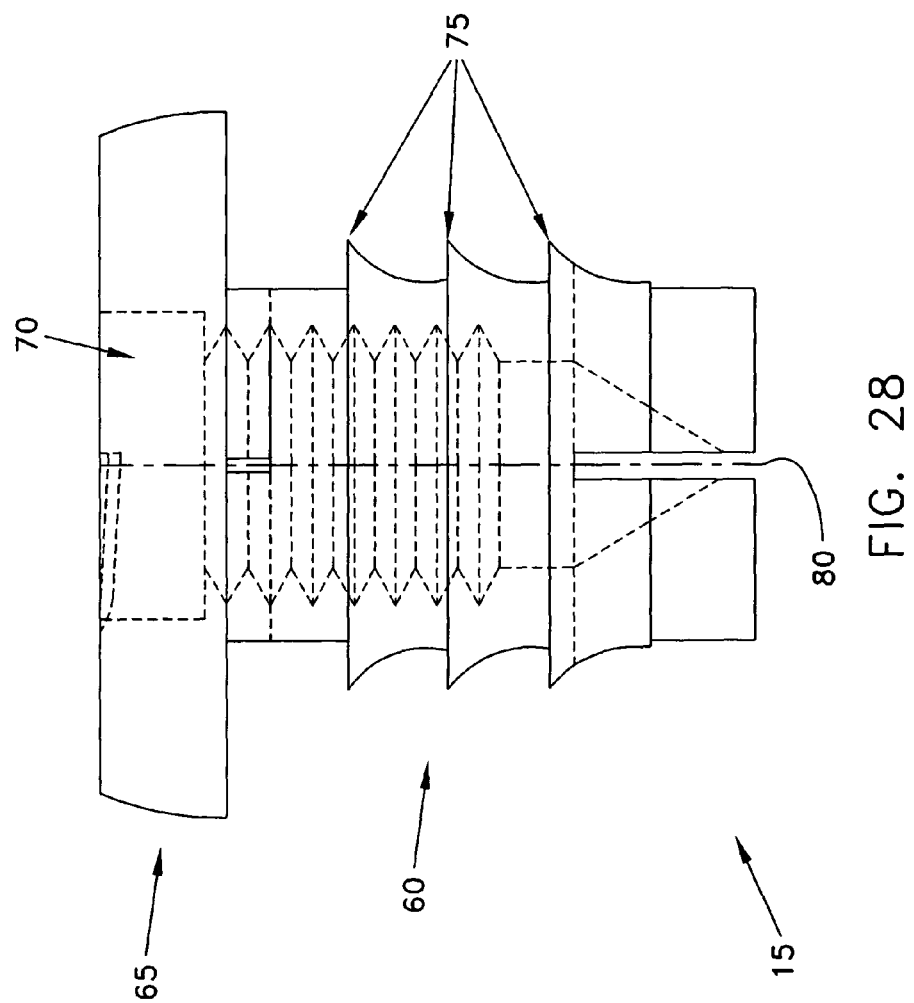

By way of further example but not limitation, sleeve 15 might be formed with ribs (or other lateral projections) 75 instead of a screw thread 75. See, for example, FIGS. 26-28, which show a sleeve 15 formed with ribs 75. In this case, sleeve 15 might be set with a mallet driver, etc., rather than with a rotational driver. Where sleeve 15 is formed with ribs 75, ribs 75 may be given a profile to facilitate insertion and impede withdrawal from the bone, e.g., sloped leading edges 135 and sharp rims 140.

Figure 29:
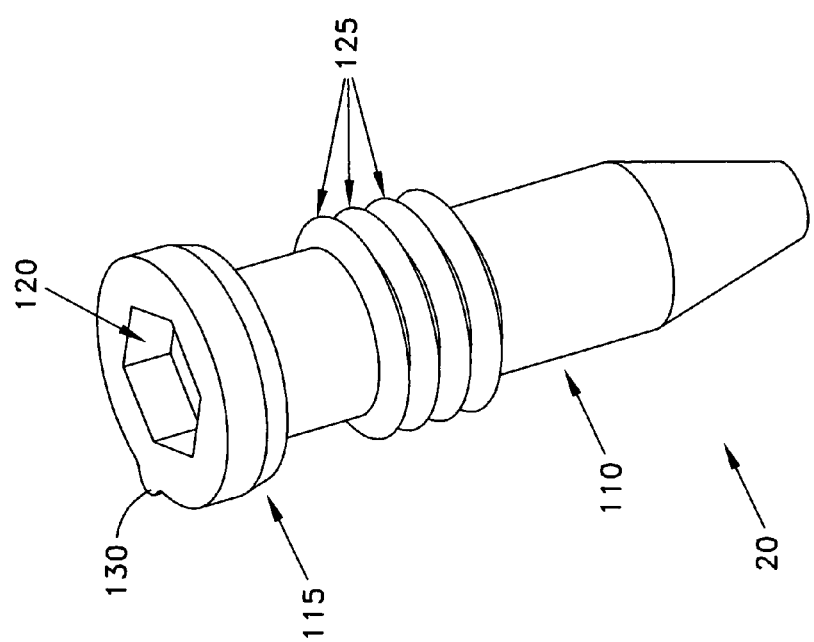
FIG. 29 is a schematic view showing another preferred form of the screw.

Also by way of example but not limitation, screw 20 may be sized to terminate within sleeve 15 rather than extend out the end of sleeve 15. Furthermore, screw thread 125 of screw 20 might be replaced by ribs (or other lateral projections) 125 for engaging the interior side wall of sleeve 15. See, for example, FIG. 29, which shows such a ribbed construction. In this case, or in other cases, the interior side wall of sleeve 15 might not be threaded. Additionally, screw 20 can be cannulated, so as to facilitate delivery over a guidewire.

Furthermore, sleeve 15 might be formed without a counterbore, and screw 20 might be formed without an enlarged head, in which case the screw would essentially constitute a threaded pin to be seated within a sleeve bore.

Additionally, the positions of detent 105 and finger 130 may be reversed, i.e., finger 130 may be formed on sleeve 15 and detent 105 may be formed on screw 20. Additionally, more than one detent and/or finger may be provided, e.g., the apparatus may comprise one finger and multiple detents.

Also, screw 20 and sleeve 15 may be pre-assembled (either at the time of manufacture or in the operating room) so as to constitute a single unit.

It should also be appreciated that the present invention may be used to secure a rod (or the like) to bone. By way of example but not limitation, the rod could be a spinal rod (or other surgical rod) used to stabilize a plurality of vertebral bodies relative to one another. In this case, a portion of the rod might be modified so as to be analogous to plate 10 (e.g., so as to provide one or more openings 35 through the rod for receiving a sleeve 15 and screw 20). See FIG. 30, where a rod 141 is provided with one or more openings 35 therethrough. Where the rod has a relatively narrow diameter, and looking now at FIG. 31, a portion of rod 141 might be flattened and/or laterally expanded so as to provide an enlarged surface area 142 for receiving openings 35 to receive sleeve 15. However, where the rod has a relatively large diameter, openings 35 may be formed in the rod without requiring any flattening and/or lateral expansion of the rod.

Figure 32:
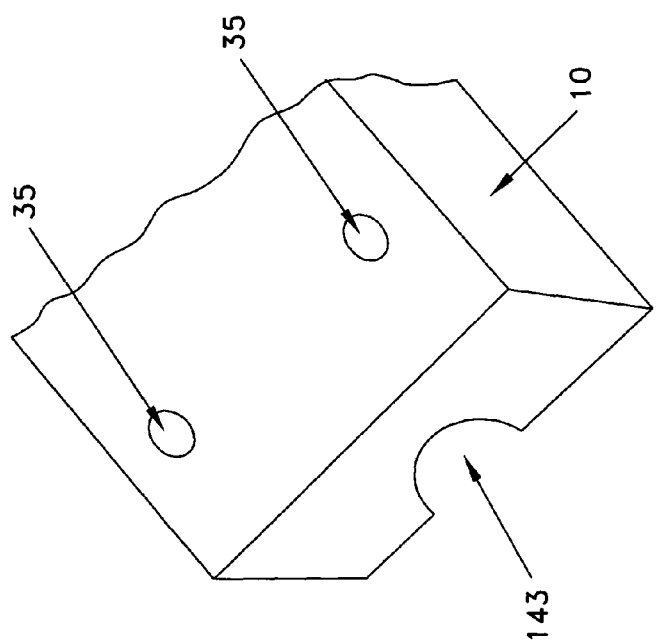
FIG. 32 is a schematic view of a plate for capturing a rod against bone.

Alternatively, an adapter might be provided to secure the rod to bone. In this case, and looking now at FIG. 32, plate 10 could function as a rod mount, preferably with a groove 143 on the underside of the plate to capture the rod to the bone. In this case, it may be necessary to position openings 35 in plate 10 so that a sleeve 15 passing through openings 35 will pass alongside a rod captured in the groove. See FIG. 32.

Figure 33:
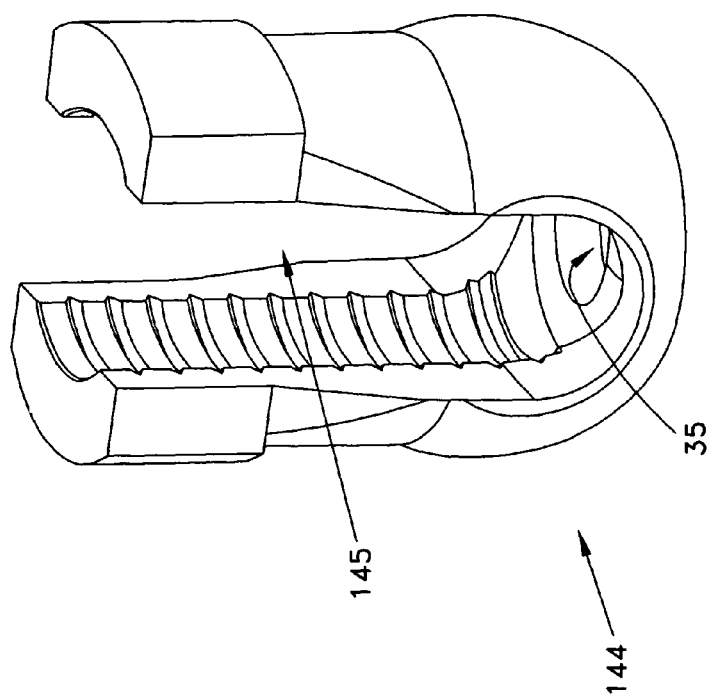
FIG. 33 is a schematic view of a "tulip" mount which may be secured to a bone using the sleeve/screw construction of the present invention.

Additionally, the novel sleeve/screw construction can be used to secure a tulip-shaped mount to the bone, with the tulip-shaped mount being used to secure a rod to the bone. More particularly, and looking now at FIG. 33, a tulip-shaped mount 144 is shown, wherein the tulip-shaped mount has an opening 35 for securing the tulip-shaped mount to bone and a slot 145 for receiving a rod.

Figure 34:
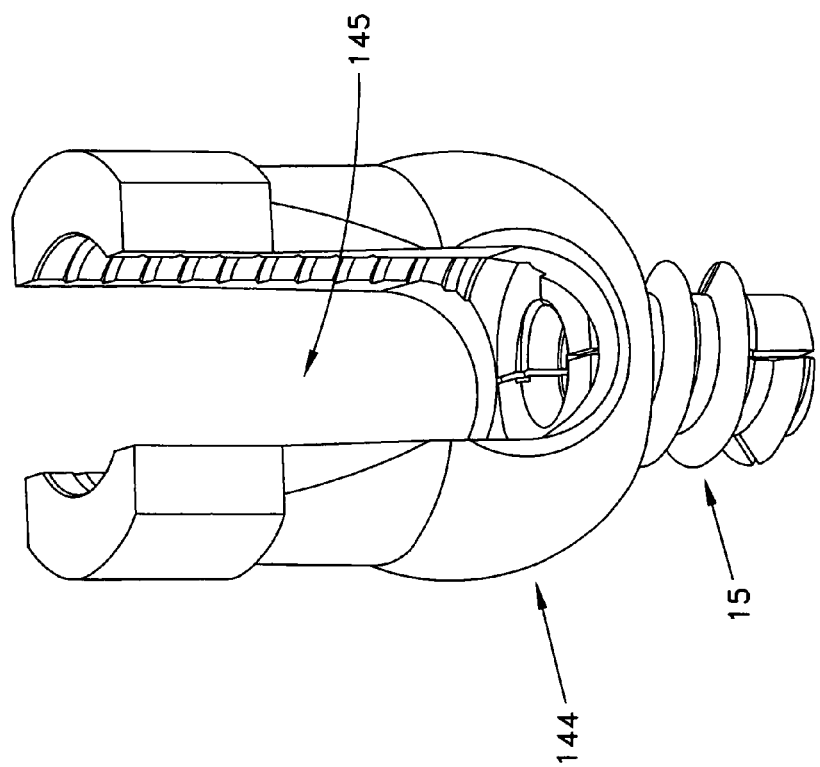
FIGS. 34 and 35 show the sleeve being mated with the tulip mount, and the screw being mated with the sleeve, respectively.
Figure 35:
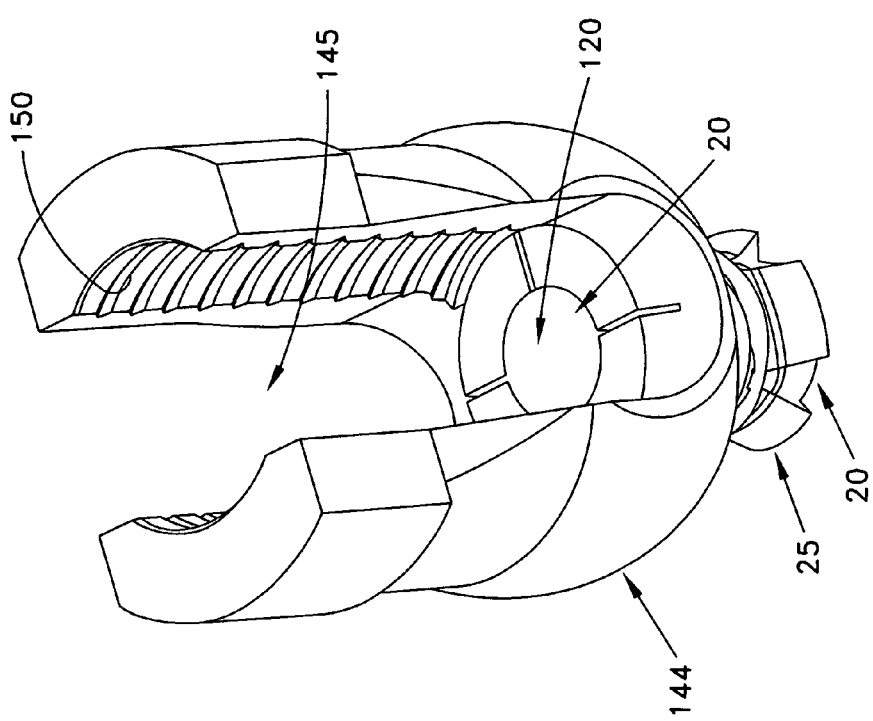

In use, tulip-shaped mount 144 is positioned alongside bone. A hole is drilled in the bone via opening 35 formed in tulip-shaped mount 144. Sleeve 15 is advanced through opening 35 (FIG. 34) and into the hole formed in the bone. Next, screw 20 is advanced through sleeve 15, causing sleeve 15 to be radially expanded, so that the sleeve is simultaneously secured to both the bone and to tulip-shaped mount 144 (see FIG. 35). With tulip-shaped mount 144 secured to the bone, a rod may be positioned in the slot 145 of tulip-shaped mount 144, whereby to stabilize the bone(s). If desired, tulip-shaped mount 144 may be provided with a threaded cap (not shown) which can be positioned superior to the rod using threads 150, so as to securely hold the rod in place within slot 145 of tulip-shaped mount 144.

Figure 36:
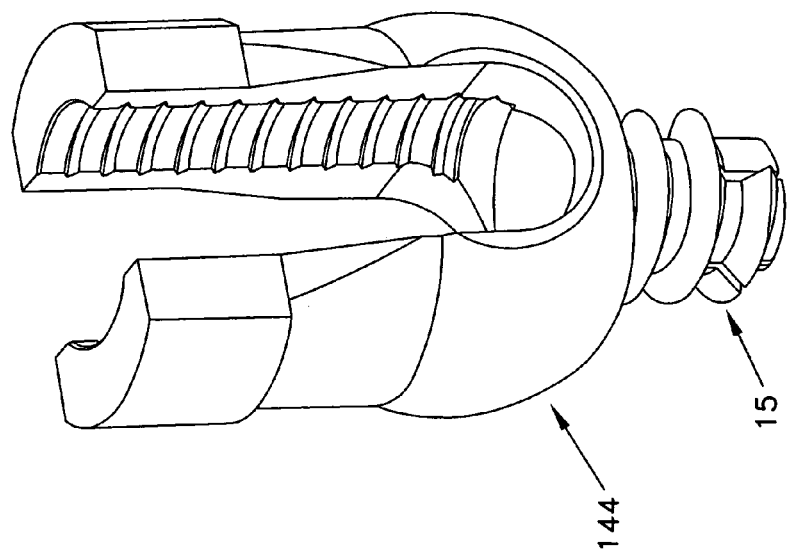
FIG. 36 is a schematic view showing a hybrid tulip mount/sleeve construction.
Figure 37:
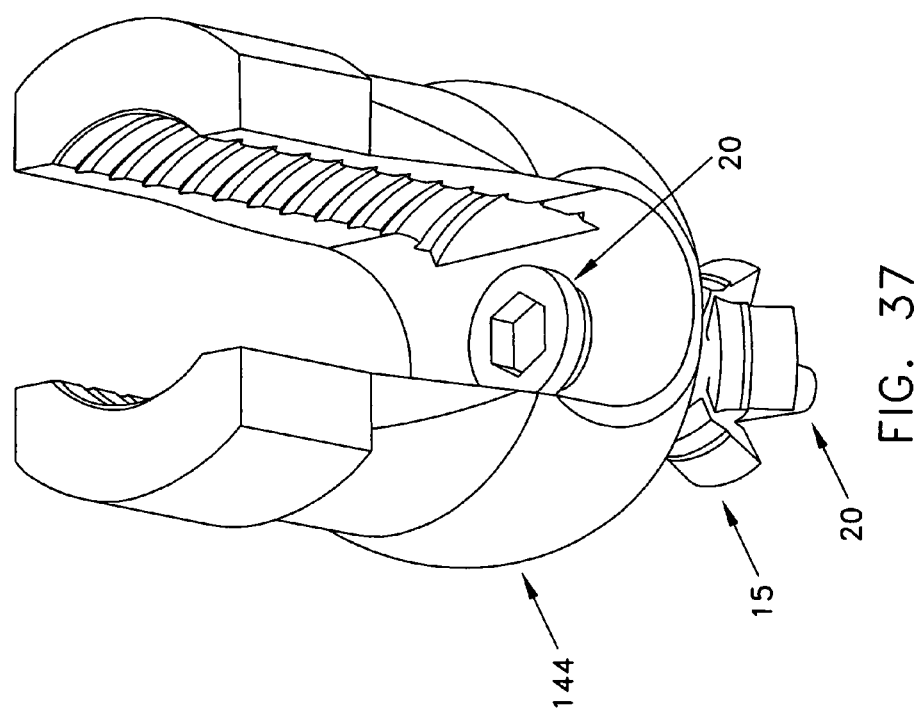
FIG. 37 is a schematic view showing a screw being mated with the hybrid tulip mount/sleeve construction shown in FIG. 36.
Figure 38:
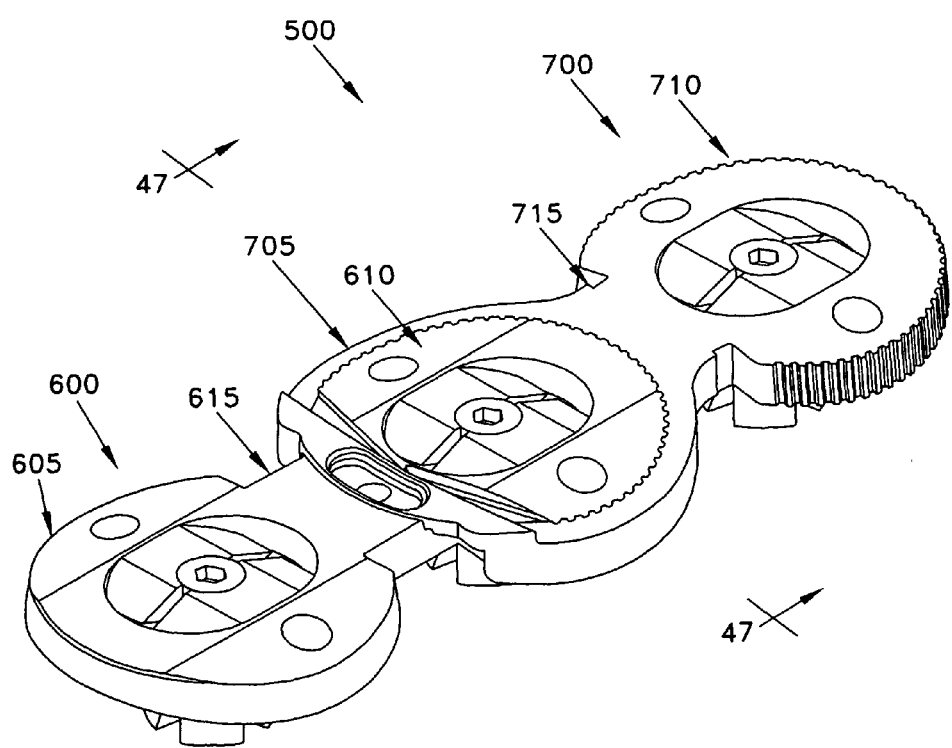
FIG. 38 is a schematic top perspective view illustrating (i) a primary anterior cervical plate (ACP) formed in accordance with the present invention, and (ii) a supplemental ACP formed in accordance with the present invention.

Looking next at FIGS. 36 and 37, it should also be appreciated that sleeve 15 can be formed integral with tulip-shaped mount 144.

Method and Apparatus for Stabilizing Bone

In many situations it may be necessary, or desirable, to stabilize bone. By way of example but not limitation, where a bone is fractured, it may be desirable to stabilize the bone with a bone plate which extends across the fracture line. By way of further example but not limitation, where two separate bones need to be secured together (e.g., in the case of a spinal fusion), it may be desirable to secure the bones to one another with a bone plate which extends from one bone to the other. In some cases, bridging or spacer material (e.g., allograft, autograft, biologic, etc.) may be placed as a graft between the two bones to stabilize and/or to enhance the fusion process of the two bones being secured together. Furthermore, in some situations (e.g., multi-level spinal surgery), it may be desirable to secure together more than two bones (e.g., in 3-level spinal surgery, it may be desirable to secure together three separate vertebral bodies). Again, bridging or spacer material may be placed as a graft between the individual bones.

In all of the foregoing situations, as well as in many other situation's which are well known to those skilled in the art, a plate or plates generally need to be secured to bone. Such securement is most commonly effected by using a surgical screw which passes through a hole in the plate and into the bone.

When using a surgical screw to secure a plate to bone, the plate is first aligned with the bone. Then a hole is drilled into the bone, by passing a drill through the pre-existing hole in the plate and into the bone. Next, the hole may be tapped. Then the surgical screw is screwed through the plate and into the hole in the bone.

Many different bone plates have been developed. In general, the configuration of these bone plates depends on their use, e.g., a fracture fixation plate may have one configuration, a spinal fusion plate may have another configuration, etc. Typically, the plate configuration seeks to balance anatomical configurations, anatomical loads, etc.

Over the past decade or so, anterior cervical fusion (ACF) has gained wide spread acceptance in the spinal community. In general, this procedure involves fusing together two (1-level) or more (multi-level) vertebral bodies. Anterior cervical plates (ACPs) are commonly used to hold the vertebral bodies in position while bone fusion occurs.

Current ACPs all suffer from one or more disadvantages, including configurations which do not adequately accommodate anatomical limitations, designs which do not adequately stabilize anatomical loads, etc. Furthermore, current ACPs are not designed to accommodate subsequent surgeries where additional levels of fixation must be added. By way of example, current ACPs are not designed to facilitate converting a 1-level fixation to a 2-level fixation.

The present invention is intended to provide a new and improved ACP which improves upon the limitations of the prior art, including providing (i) improved anatomical accommodation, (ii) improved load stabilization, (iii) optional future level extensions, etc.

The present invention is intended to address the foregoing deficiencies of the prior art by providing a new and improved method and apparatus for stabilizing bone in general, and vertebral bodies in particular.

Among other things, the present invention provides a new and improved ACP system for stabilizing two or more cervical bodies.

In one preferred form of the present invention, the new ACP system comprises a plate which is to be attached to two adjacent cervical bodies, and attachment apparatus for attaching the ACP to the two cervical bodies. Preferably, the attachment apparatus comprise a screw and, in one preferred form of the invention, the attachment apparatus comprise a sleeve and screw combination, where the sleeve acts as an interface between (i) the bone and the screw, and (ii) the ACP and the screw, with the sleeve enhancing fixation. Among other things, the ACP is specifically configured to provide the option of adding future level extensions.

Looking now at FIGS. 38-46, there is shown a new and improved ACP system 500 for stabilizing two or more cervical bodies relative to one another. ACP system 500 generally comprises a primary ACP 600 for effecting a 1-level stabilization, and may further comprise one or more supplemental ACPs 700 for effecting subsequent 1-level stabilizations. Thus, for example, where a 1-level stabilization is to be initially established, and a further 1-level stabilization is to be thereafter established, ACP system 500 may comprise a primary ACP 600 and a secondary ACP 700, whereby to collectively establish the desired 2-level stabilization.

Figure 39:
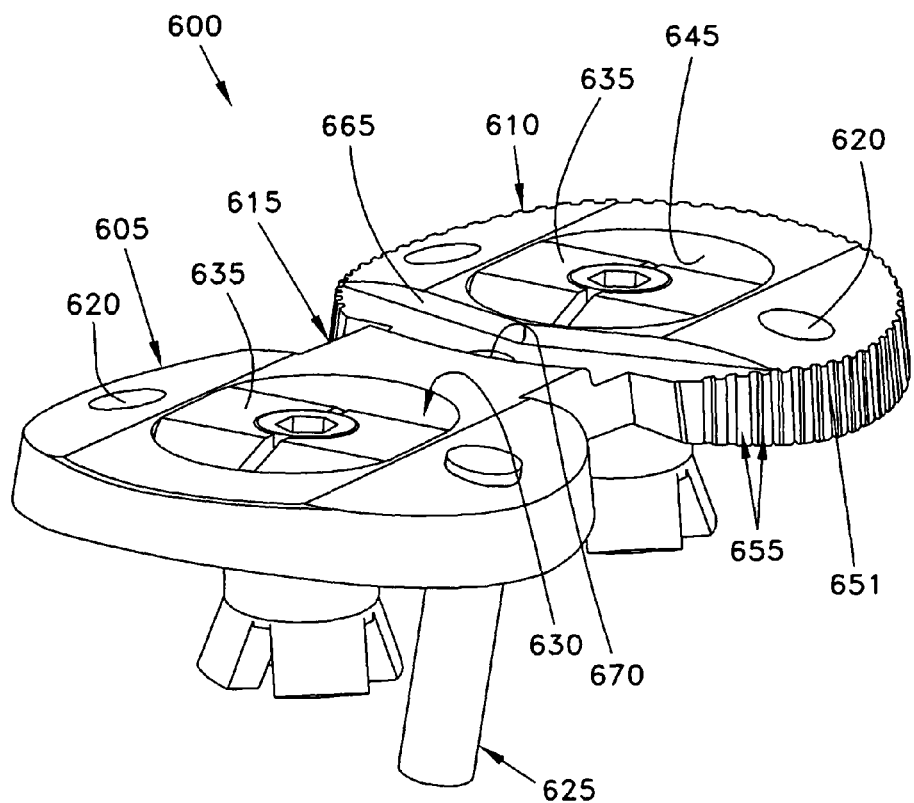
FIG. 39 is an enlarged schematic top perspective view illustrating the primary ACP shown in FIG. 38.

Looking now at FIG. 39, primary ACP 600 generally comprises a first, generally toroidal body 605, a second generally toroidal body 610, and a bridge 615 connecting first generally toroidal body 605 to second generally toroidal body 610. First toroidal body 605 and second toroidal body 610 each include (i) at least one opening 620 for receiving a pin 625 for initially tacking primary ACP 600 to the cervical bodies, and (ii) at least one opening 630 for receiving attachment apparatus 635 for thereafter securing primary ACP 600 to the cervical bodies.

Attachment apparatus 635 may comprise a spinal screw. More preferably, however, attachment apparatus 635 comprise a sleeve and screw combination of the sort discussed above (i.e., sleeve 15 and screw 20) and/or as disclosed in one or more of: (i) pending prior U.S. patent application Ser. No. 10/246,304, filed Sep. 18, 2002 by Barry T. Bickley for FIXATION AUGMENTATION DEVICE AND RELATED TECHNIQUES; (ii) pending prior U.S. patent application Ser. No. 10/554,379, filed Oct. 25, 2005 by Barry T. Bickley et al. for FIXATION AUGMENTATION DEVICE AND RELATED TECHNIQUES; and/or (iii) pending prior U.S. patent application Ser. No. 12/148,845, filed Apr. 23, 2008 by Barry T. Bickley et al. for METHOD AND APPARATUS FOR SECURING AN OBJECT TO BONE. These three patent applications are hereby incorporated herein by reference.

Figure 53:
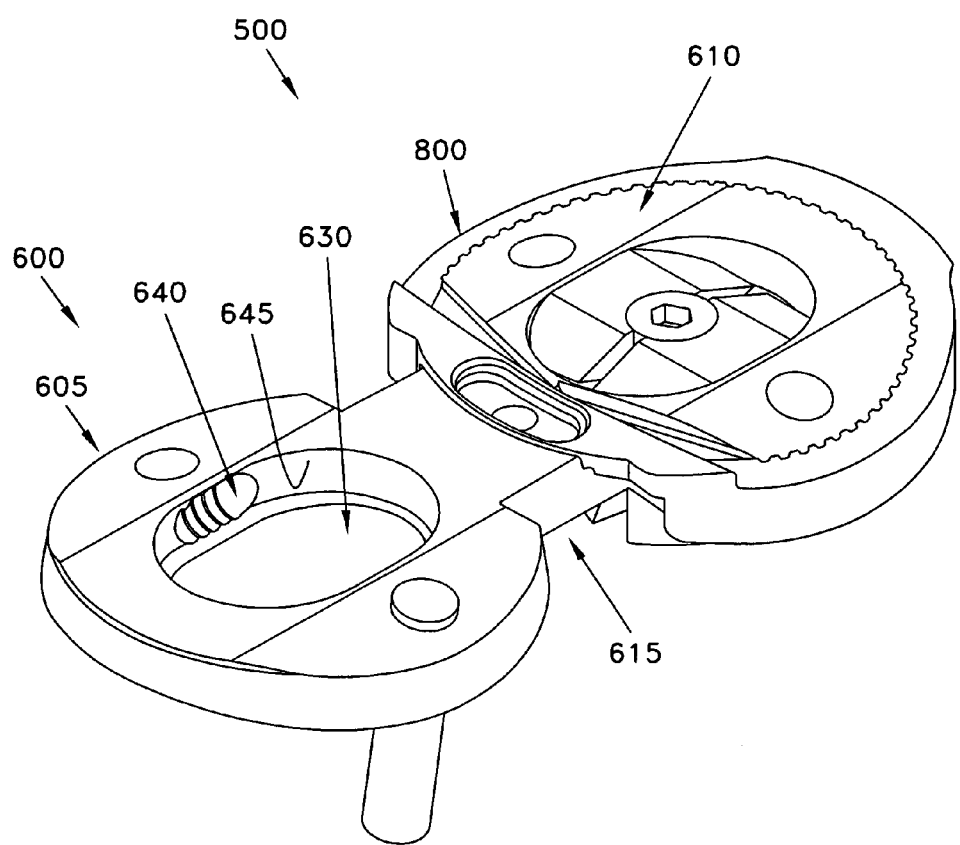
FIG. 53 is a schematic top perspective view illustrating a primary ACP 600 with a protective collar attached.

Preferably, primary ACP 600 includes recesses 640 (FIG. 53) formed in the sidewalls 645 which define openings 630. Recesses 640 help to releasably secure attachment apparatus 635 within openings 630, i.e., by receiving fingers 650 (FIG. 40) formed on the proximal end of attachment apparatus 635.

In order to facilitate the use of primary ACP 600 in conjunction with a supplemental ACP 700:
(i) the outer sidewall 651 forming the periphery of second toroidal body 610 is preferably formed with a taper (FIG. 47) in order to mate with a corresponding opening in supplemental ACP 700, as will hereinafter be discussed in further detail below;
(ii) primary ACP 600 preferably includes a plurality of teeth 655 extending along outer sidewall 651 of second toroidal body 610, in order to selectively lock primary ACP 600 to a supplemental ACP, as will hereinafter be discussed in further detail below;
(iii) primary ACP 600 is preferably cut back on its lateral edges, adjacent to where second toroidal body 610 meets bridge 615, i.e., at 660 (FIG. 41), in order to allow primary ACP 600 and a supplemental ACP 700 to assume a wide range of different positions, as will hereinafter be discussed in further detail below;
(iv) primary ACP 600 is preferably cut back on its proximal face, adjacent to where second toroidal body 610 meets bridge 615, i.e., at 665, in order to mate with a corresponding portion of a supplemental ACP 700, as will hereinafter be discussed in further detail below; and
(v) primary ACP 600 includes an opening 670 formed in its proximal face, to facilitate locking primary ACP 600 and a supplemental ACP 700, as will hereinafter be discussed in further detail.

Figure 40:
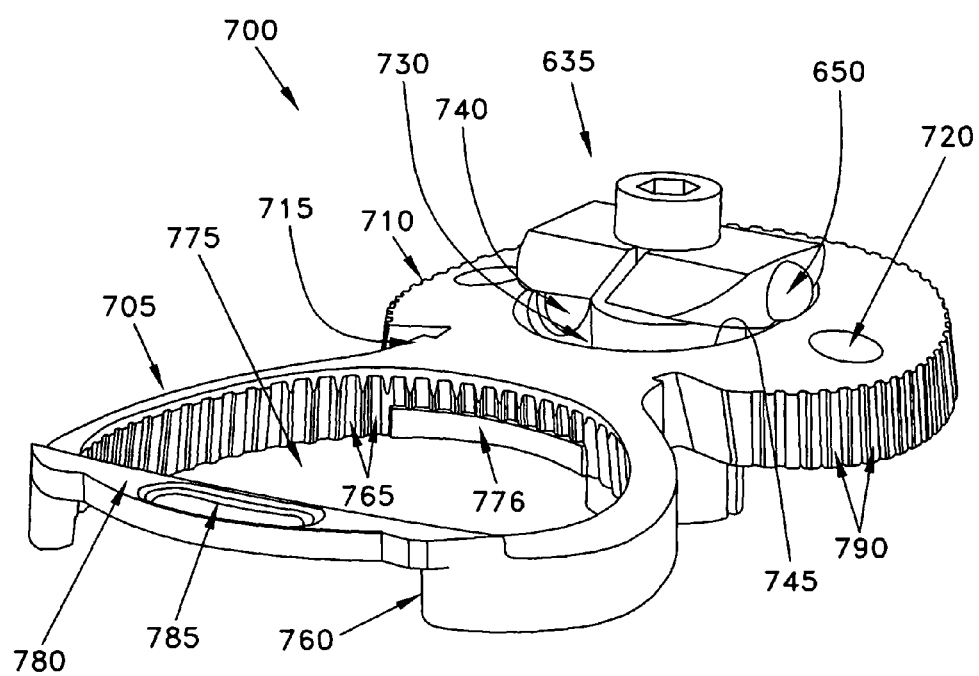
FIG. 40 is an enlarged schematic top perspective view illustrating the supplemental ACP shown in FIG. 38.
Figure 41:
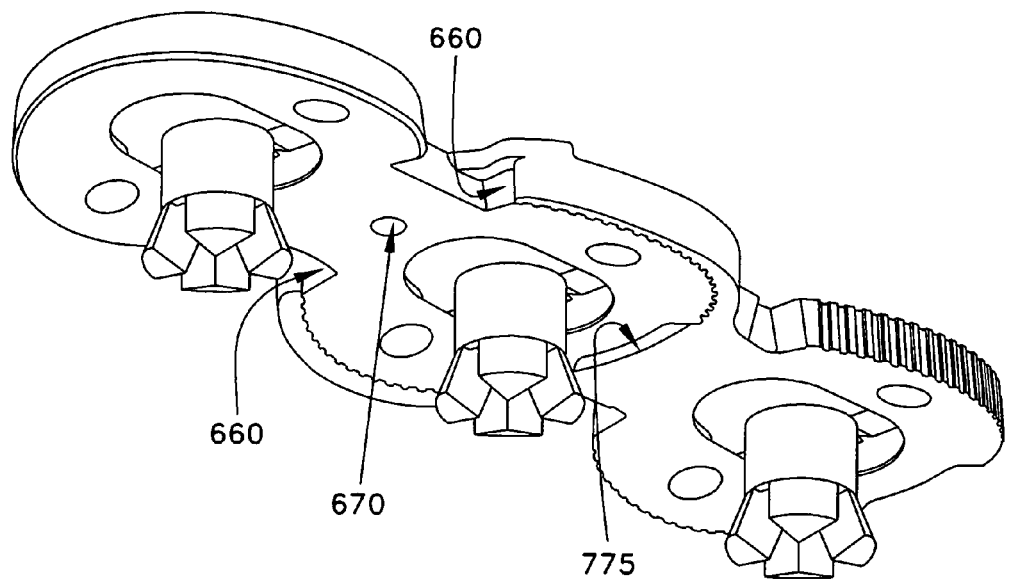
FIG. 41 is a schematic bottom perspective view illustrating the primary ACP and the supplemental ACP shown in FIG. 38.
Figure 42:
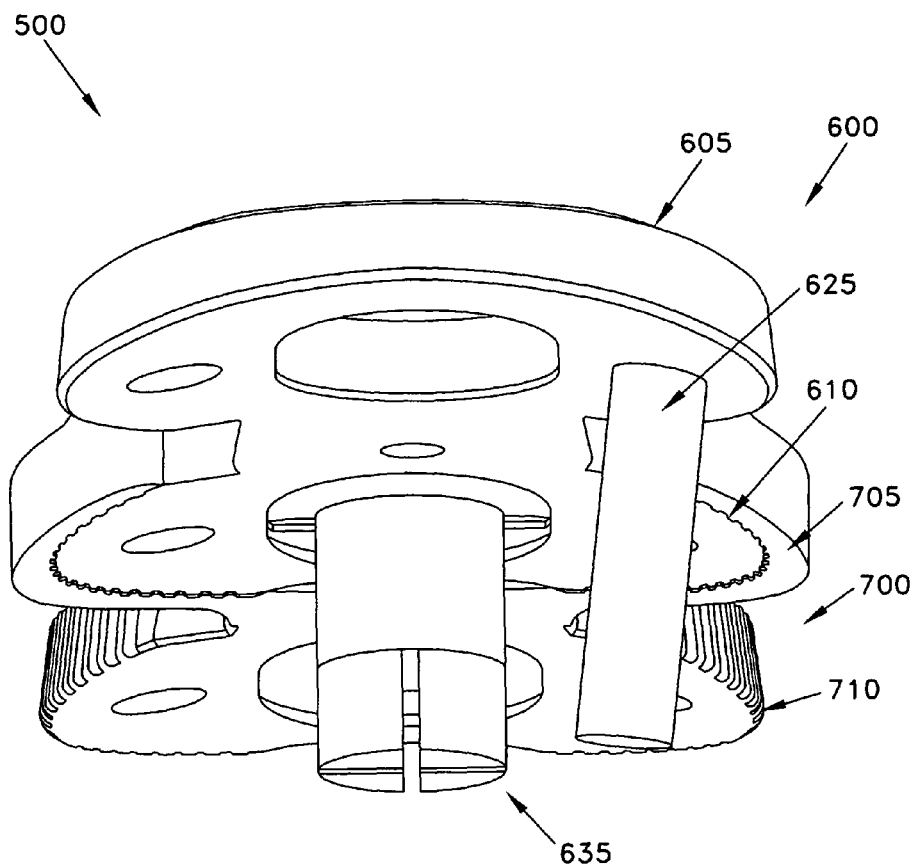
FIG. 42 is a schematic end perspective view illustrating the primary ACP and the supplemental ACP shown in FIG. 38.
Figure 43:
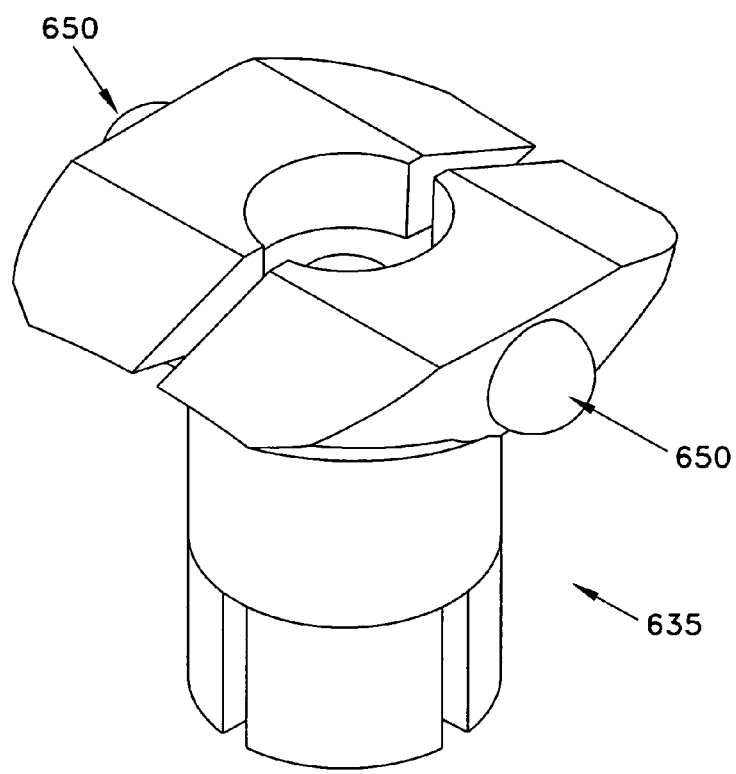
FIGS. 43-46 are schematic views of the preferred form of attachment apparatus used to secure the primary ACP and the supplemental ACP to bone.
Figure 44:
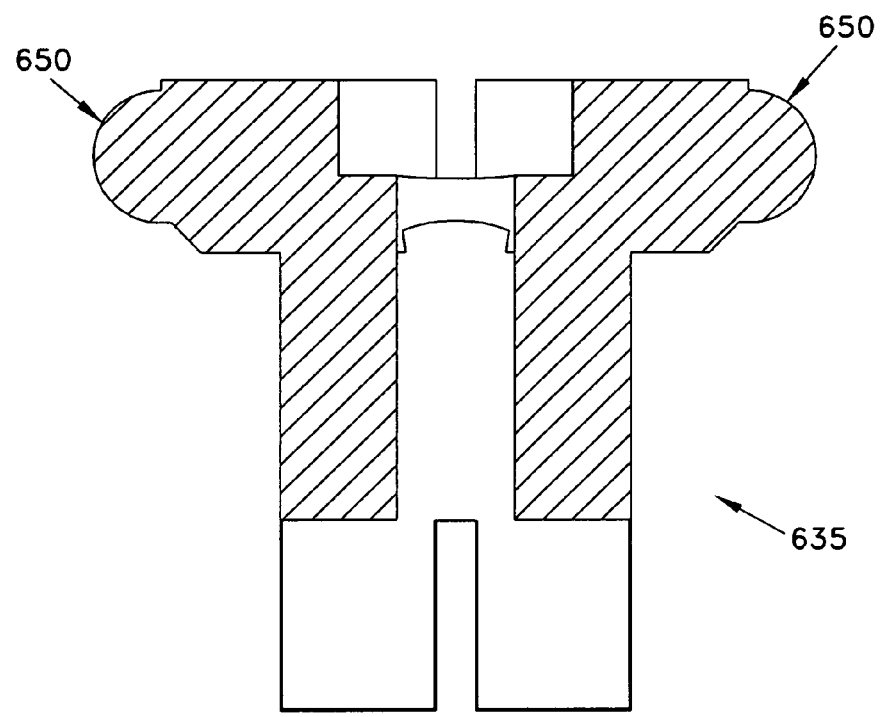
Figure 45:
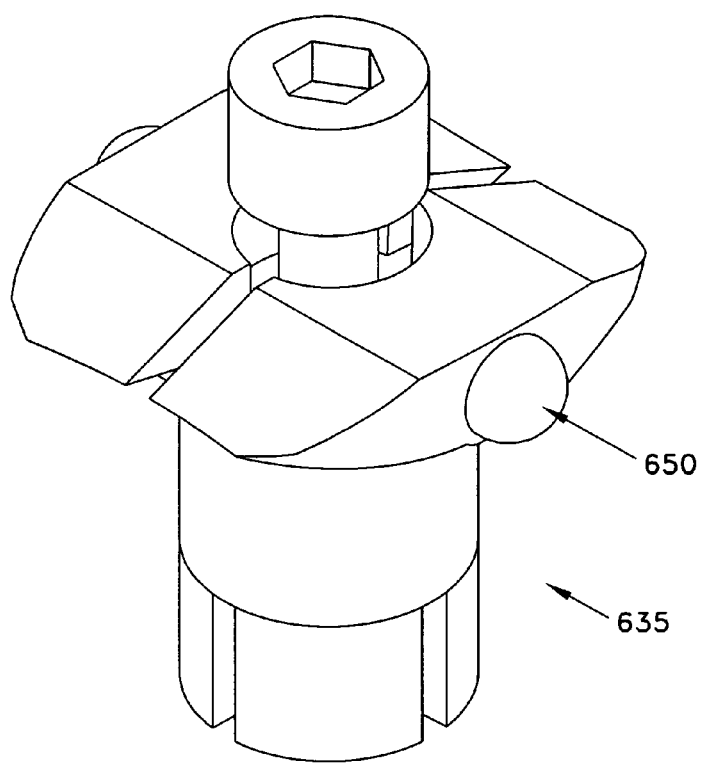
Figure 46:
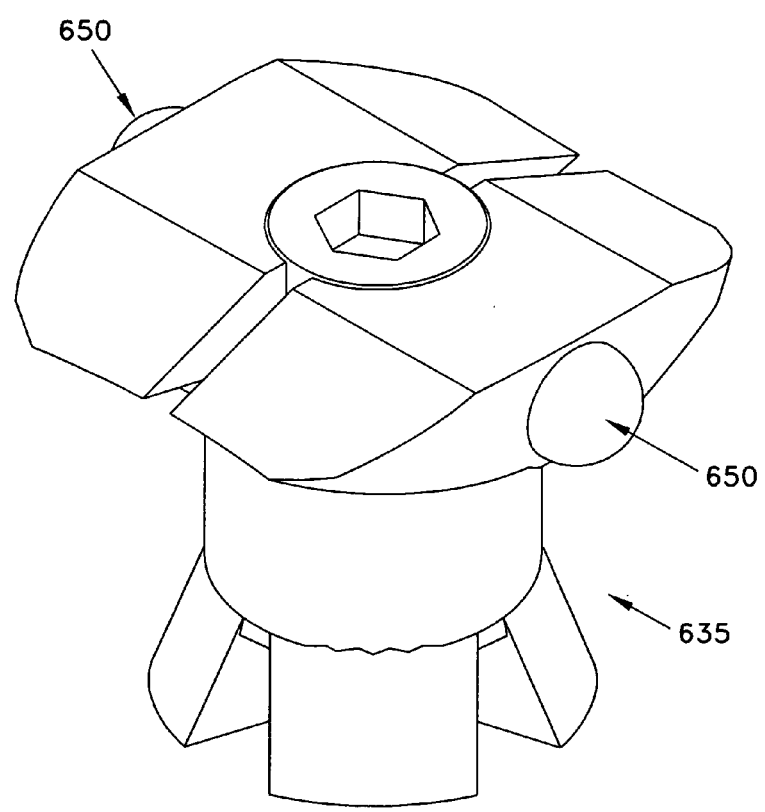

Looking now at FIG. 40, supplemental ACP 700 generally comprises a first, generally toroidal body 705, a second generally toroidal body 710, and a bridge 715 connecting first generally toroidal body 705 to second generally toroidal body 710. Second toroidal body 710 includes (i) at least one opening 720 for receiving a pin (not shown) for initially tacking supplemental ACP 700 to a cervical body, and (ii) at least one opening 730 for receiving attachment apparatus 635 for thereafter securing supplemental ACP 700 to a cervical body.

Again, attachment apparatus 635 may comprise a spinal screw. More preferably, however, attachment apparatus 635 comprise a sleeve and screw combination of the sort discussed above (i.e., sleeve 15 and screw 20) and/or as disclosed in one or more of: (i) pending prior U.S. patent application Ser. No. 10/246,304; (ii) pending prior U.S. patent application Ser. No. 10/554,379; and/or (iii) pending prior U.S. patent application Ser. No. 12/148,845.

Preferably, supplemental ACP 700 includes recesses 740 formed in the sidewalls 745 which define opening 730. Recesses 740 help to releasably secure attachment apparatus 635 within openings 730, i.e., by receiving fingers 650 formed on the proximal end of attachment apparatus 635.

In order to facilitate use of supplemental ACP 700 with primary ACP 600:
(i) supplemental ACP 700 preferably includes a large opening 775 formed in its first toroidal body 705, and the sidewall 776 defining opening 775 is preferably formed with a taper (FIG. 47), in order to mate with the correspondingly-tapered second toroidal body 610 of primary ACP 600, as will hereinafter be discussed in further detail below;
(ii) supplemental ACP 700 preferably includes a plurality of teeth 765 lining at least a portion of opening 775, in order to selectively lock primary ACP 600 to a supplemental ACP, as will hereinafter be discussed in further detail below;
(iii) supplemental ACP 700 preferably has its first toroidal body 705 cut back adjacent to its free end, i.e., at 760, in order to allow primary ACP 600 and a supplemental ACP 700 to assume a wide range of different positions, as will hereinafter be discussed in further detail below; and
(iv) supplemental ACP 700 preferably includes strap 780 on its first toroidal body 705, with strap 780 including a slot 785, to facilitate locking primary ACP 600 and a supplemental ACP 700, as will hereinafter be discussed in further detail.

In use, primary ACP 600 is initially used to establish 1-level cervical stabilization. This is done by first positioning the two cervical bodies in the desired position, with or without bridging or spacer material (e.g., allograft, autograft, biologic, etc.) being placed as a graft between the two bones to stabilize and/or to enhance the fusion process of the two bones being secured together. Then primary ACP 600 is positioned against the two cervical bodies, with first toroidal body 605 of primary ACP 600 being positioned against one cervical body, and second toroidal body 610 of primary ACP 600 being positioned against a second cervical body. Primary ACP 600 is then pinned to the two bodies, i.e., using pins 625 extending through openings 620. Alternatively, primary ACP 600 may be pinned to one of the two bodies, the positioning of the two bodies may then be adjusted, and then the primary ACP pinned to the other of the two bodies. Thereafter, primary ACP 600 is secured to the two cervical bodies by passing attachment apparatus 635 through openings 630. By forming the head of attachment apparatus 635 with a hemispherical profile, and by forming the sidewalls of openings 630 with a corresponding arced profile, attachment apparatus 635 can be set at a range of angles "off the perpendicular" in order to accommodate various surgical considerations, e.g., patient anatomy, load distribution, etc. Furthermore, by forming the head of attachment apparatus 635 with a reduced profile (see FIGS. 38 and 43), attachment apparatus 635 will present a lower profile to the surrounding tissue if and when attachment apparatus 635 are set "off the perpendicular".

In addition to the foregoing, by using attachment apparatus 635 in the form of a sleeve and screw combination of the sort discussed above (i.e., sleeve 15 and screw 20) and/or as disclosed in one or more of (i) pending prior U.S. patent application Ser. No. 10/246,304; (ii) pending prior U.S. patent application Ser. No. 10/554,379; and/or (iii) pending prior U.S. patent application Ser. No. 12/148,845, a significant advantage is obtained. More particularly, by using attachment apparatus 635 of this type, the sleeve is effectively interposed between the screw and the ACP. Thus, it is the sleeve which is loaded by the ACP and therefore there is no transfer of motion forces directly onto the screw. As a result, there is a reduced tendency for the screw to back out over time.

Figure 47:
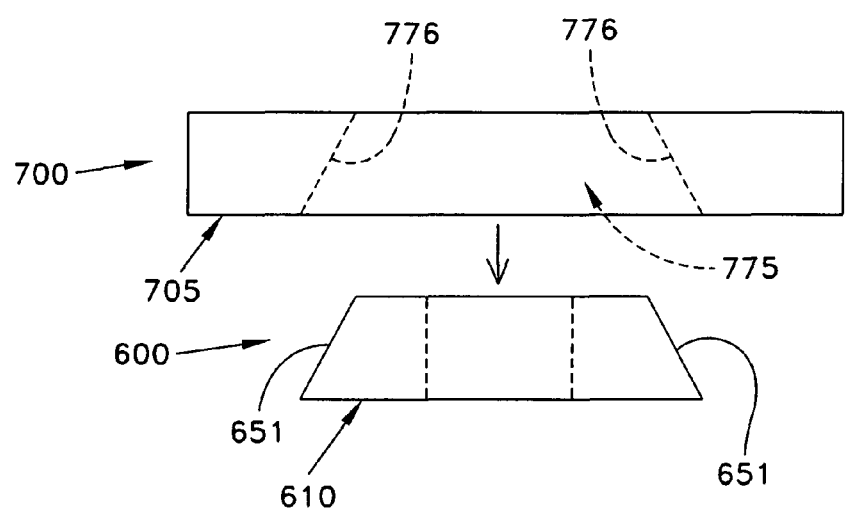
FIG. 47 is a schematic side view showing how a supplemental ACP 700 fits over the primary ACP 600.

If and when the 1-level stabilization of primary ACP 600 needs to be extended to a 2-level stabilization, a supplemental ACP 700 is used. More particularly, and looking still at the figures, first toroidal body 705 of supplemental ACP 700 is fit over second toroidal body 610 of primary ACP 600, with second toroidal body 610 of primary ACP 600 being received in large opening 775 (FIG. 41) of first toroidal body 705 of supplemental ACP 700. Seating of second toroidal body 610 of primary ACP 600 in large opening 775 of supplemental ACP 700 is facilitated by complementary tapered surfaces 651, 776 (FIG. 47). Furthermore, by forming primary ACP 600 with surfaces 651 which taper inwardly as they move away from the bone, and by forming supplemental ACP 700 with surfaces 776 which taper outwardly as they move toward the bone, fitting supplemental ACP 700 over primary ACP 600 will help clear away any tissue which may have grown over the primary ACP while it has been implanted (e.g., in a revision situation). As second toroidal body 610 of primary ACP 600 is received in large opening 775 (FIG. 41) of first toroidal body 705 of supplemental ACP 700, teeth 655 of primary ACP 600 engage with teeth 765 of supplemental ACP 700 so as to fix the two bodies relative to one another, with strap 780 of supplemental ACP 700 overlying bridge 615 of primary ACP 600. Then a screw (not shown) is passed through slot 785 in bridge 780 (FIG. 38) and into opening 670 in bridge 615 (FIG. 39), whereby to lock primary ACP 600 and supplemental ACP 700 into position relative to one another. Thereafter, supplemental ACP 700 is secured to the third cervical body by passing attachment apparatus 635 through opening 730. By forming the head of attachment apparatus 635 with a hemispherical profile, and by forming the sidewalls of openings 730 with a corresponding arced profile, attachment apparatus 635 can be set at a range of angles "off the perpendicular" in order to accommodate various surgical considerations, e.g., patient anatomy, load distribution, etc. Furthermore, by forming the head of attachment apparatus 635 with a reduced profile (see FIGS. 38 and 43), attachment apparatus 635 will present a lower profile to the surrounding tissue if and when attachment apparatus 635 are set "off the perpendicular".

In addition to the foregoing; by using attachment apparatus 635 in the form of a sleeve and screw combination of the sort discussed above (i.e., sleeve 15 and screw 20) and/or as disclosed in one or more of: (i) pending prior U.S. patent application Ser. No. 10/246,304; (ii) pending prior U.S. patent application Ser. No. 10/554,379; and/or (iii) pending prior U.S. patent application Ser. No. 12/148,845, a significant advantage is obtained. More particularly, by using attachment apparatus 635 of this type, the sleeve is effectively interposed between the screw and the ACP. Thus, it is the sleeve which is loaded by the ACP and therefore there is no transfer of motion forces directly onto the screw. As a result, there is a reduced tendency for the screw to back out over time.

Figure 48:
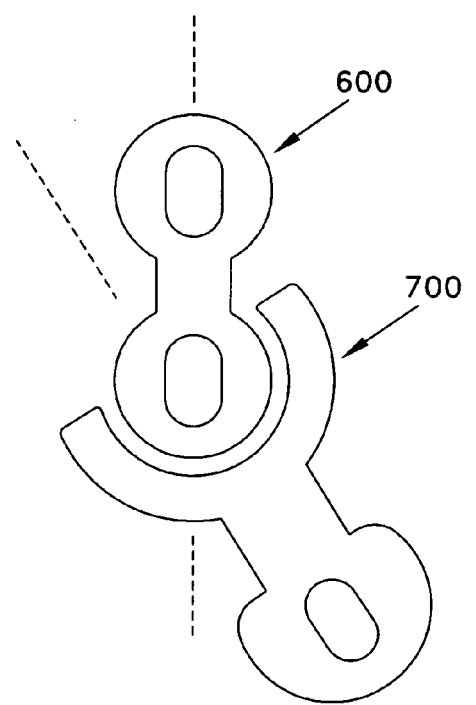
FIGS. 48 and 49 are schematic top views showing how a primary ACP 600 and a supplemental ACP 700 may be oriented "off-axis" to one another.
Figure 49:
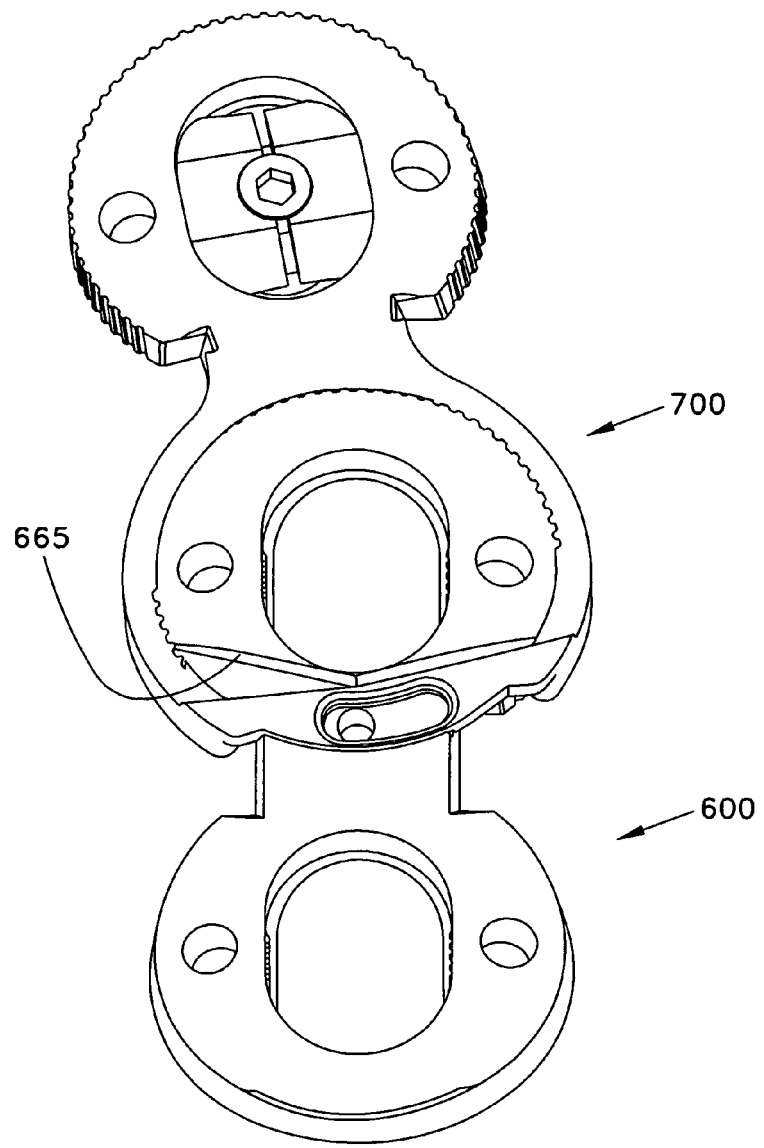

Due to the construction of primary ACP 600 and supplemental ACP 700, the primary ACP and the supplemental ACP can be aligned in a variety of orientations, i.e., on-axis (FIG. 38) or off-axis (FIGS. 48 and 49) before being secured. In essence, supplemental ACP 700 can be "dialed around" primary ACP 600, according to the particular anatomical situation encountered by the surgeon. This can be particularly helpful in revision cases, since the surgeon does not need to remove a mis-aligned primary ACP 600 in order to get proper alignment of a supplemental ACP 700.

If further levels of stabilization are required, additional supplemental ACPs 700 can be added in a serial fashion. To this end, second toroidal body 710 of supplemental ACP 700 includes teeth 790 for mating with teeth 765 of an immediately-proceeding supplemental ACP 700. Again, each incremental supplemental ACP 700 may be set on-axis or off-axis from its immediately-preceding ACP, as dictated by the existing position of the immediately-preceding ACP and by the patient anatomy being encountered.

Figure 50:
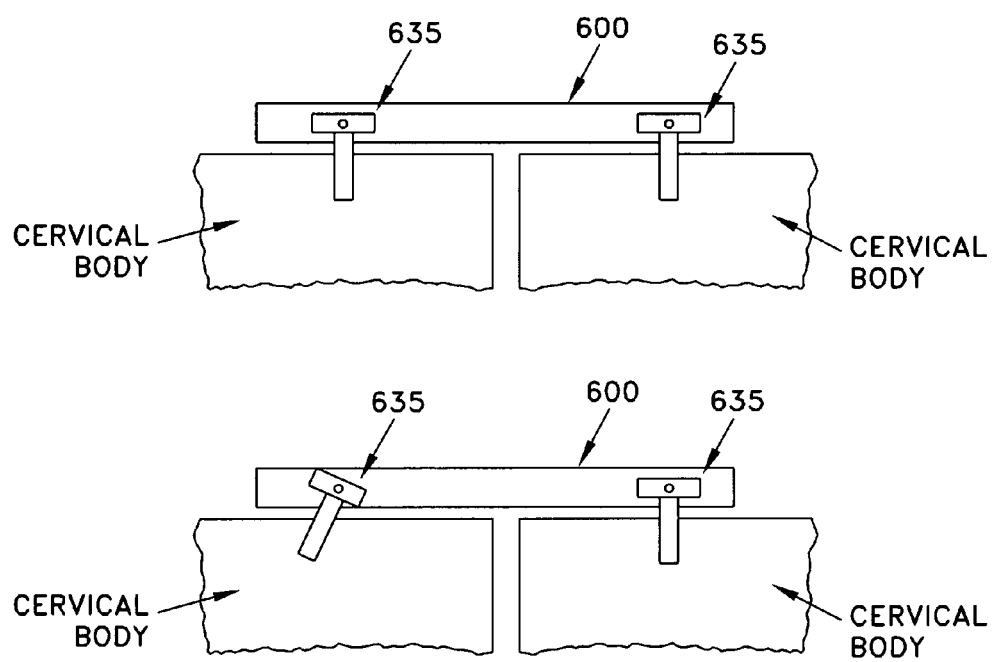
FIGS. 50 and 51 are schematic side views showing how attachment apparatus 635 may pivot relative to primary ACP 600.
Figure 51:
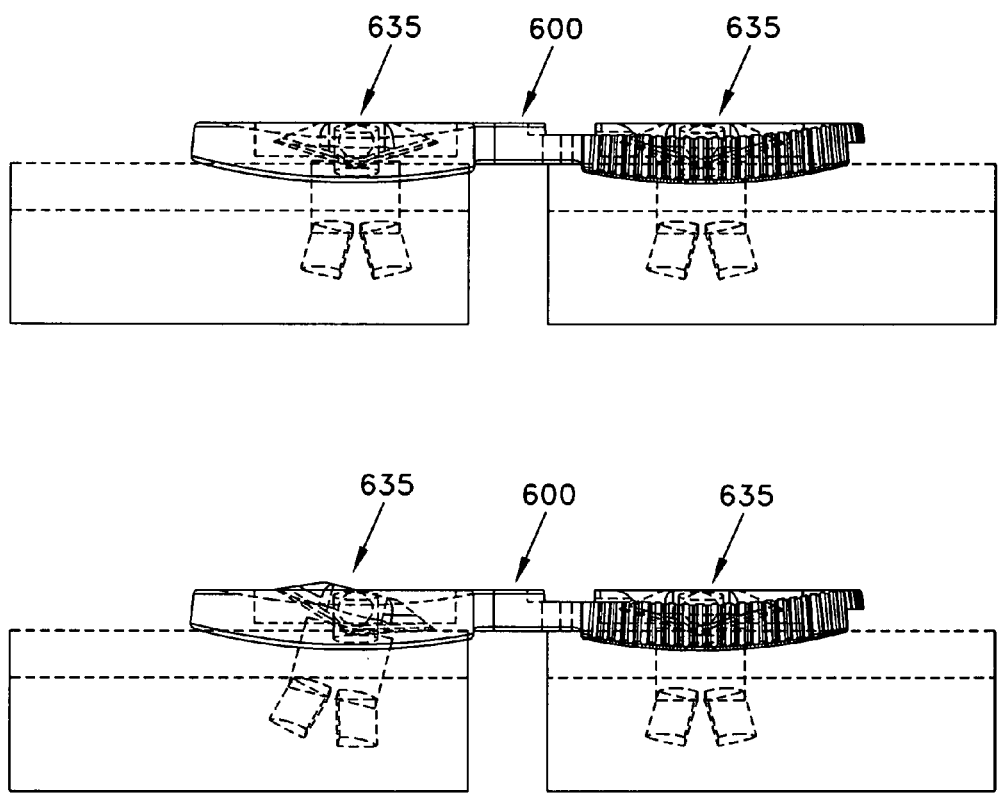

Among other things, it should be appreciated that when attachment apparatus 635 include receiving fingers 650 (FIG. 40), and when primary ACP 600 and supplemental ACP 700 include recesses 640, 740, attachment apparatus 635 are able to pivot relative to primary ACP 600 and supplemental ACP 700. This construction permits primary ACP 600 and/or supplemental ACP 700 to pivot relative to attachment apparatus 635 (and hence pivot relative to the cervical bodies receiving the distal ends of attachment apparatus 635), without permitting longitudinal and/or lateral translation of primary ACP 600 and/or supplemental ACP 700 relative to attachment apparatus 635 (and hence the cervical bodies receiving the distal ends of attachment apparatus 635). See FIGS. 50 and 51.

Alternative Constructions

If desired, primary ACP 600 may have more than one opening 630 per level, and/or supplemental ACP 700 may have more than one opening 730 per level. Furthermore, primary ACP 600 may extend for more than two levels, and/or supplemental ACP 700 may extend for more than two levels.

Furthermore, openings 630 and/or openings 730 may have a round or oval shape. The oval shape is generally preferred, since it provides an anti-rotation feature when attachment apparatus 635 comprise a sleeve and screw combination. Furthermore, the oval shape provides some opportunity for the attachment apparatus 635 to slide within the opening.

In addition to the foregoing, recesses 640 and 740 can comprise a hemisphere or an elongated slot. Where recesses 640 and 740 comprise an elongated slot, the slot can itself provide several seats to accommodate a range of engagements. By way of example but not limitation, the slot can comprise a plurality of detents spaced along the length of the slot for selectively seating fingers 650, whereby to permit adjustable engagement of attachment apparatus 635 to primary ACP 600 and supplemental ACP 700.

Figure 52:
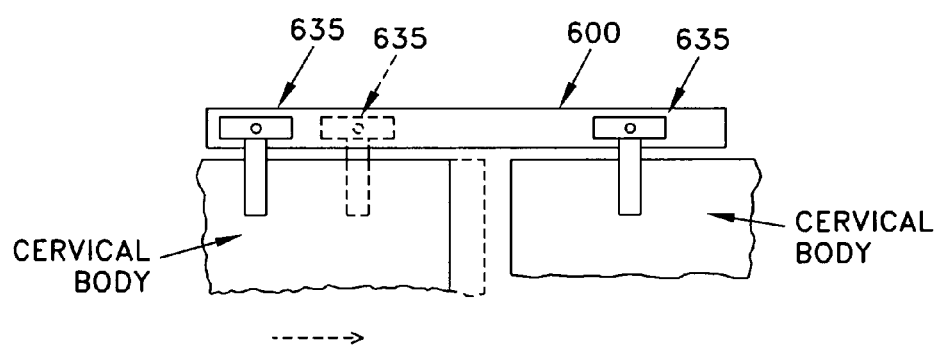
FIG. 52 is a schematic side view showing how attachment apparatus 635 may translate longitudinally relative to primary ACP 600.

By forming openings 630, 730 with an oval shape, and by forming recesses 640, 740 in a slot configuration with several seats, dynamic fixation can be effected. More particularly, the foregoing construction permits primary ACP 600 and/or supplemental ACP 700 to translate longitudinally relative to attachment apparatus 635 (and hence translate longitudinally relative to the cervical bodies receiving the distal ends of attachment apparatus 635), without permitting lateral translation of primary ACP 600 and/or supplemental ACP 700 relative to attachment apparatus 635 (and hence the cervical bodies receiving the distal ends of attachment apparatus 635). See FIG. 52.

It should also be appreciated that teeth 655 of primary ACP 600, teeth 765 of supplemental ACP 700, and teeth 790 of supplemental ACP 700 may all be replaced with facet structures. These facet structures may be configured so as to provide fast and simple alignment and assembly of adjoining ACPs.

Protective Collars

Figure 54:
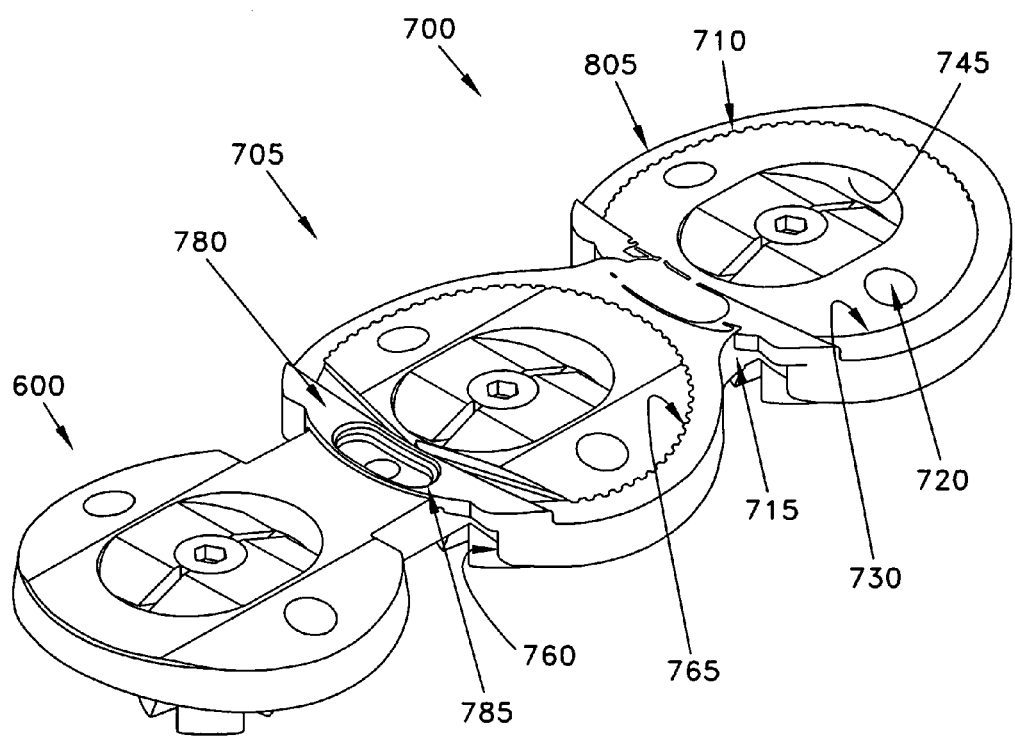
FIG. 54 is a schematic top perspective view illustrating a supplemental ACP 700 with a protective collar attached.

Primary ACP 600 and/or supplemental ACP 700 may be provided with a protective collar so as to minimize tissue ingrowth about second generally toroidal body 610 and/or second generally toroidal body 710, respectively. See, for example, FIG. 53, which shows a protective collar 800 set about second generally toroidal body 610, and FIG. 54, which shows a protective collar 805 set about second generally toroidal body 710.

Protective collars 800 and/or 805 are preferably pre-applied to primary ACP 600 and/or supplemental ACP 700, respectively, prior to deployment of the ACP into the body, although the protective collars may also be applied after an ACP has been deployed in the body.

If primary ACP 600 and/or supplemental ACP 700 is equipped with a protective collar, and if an additional level of fixation is to be added (i.e., if a supplemental ACP 700 is to be added to the ACP structure(s) already in place), that protective collar is removed before the supplemental ACP is deployed, so that the supplemental ACP can be fixed to the ACP structure(s) already in place.

Materials

The various components can be formed out of any material or materials consistent with the present invention. Thus, for example, some or all of the components may be formed out of implantable metals (e.g., surgical grade stainless steel, titanium, Nitinol, etc.), implantable plastics, implantable absorbables, etc.

Modifications

It will be understood that many changes in the details, materials, steps and arrangements of parts, which have been herein described and illustrated in order to explain the nature of the invention, may be made by those skilled in the art without departing from the principles and scope of the present invention.

What is claimed is:

1. A surgical system for stabilizing a first bone segment to a second bone segment, the system comprising:
   a plate having a first end and a second end, wherein the first end is configured to be secured to the first bone segment and the second end is configured to be secured to the second bone segment, and further wherein the plate has a structural integrity sufficient to stabilize the first bone segment to the second bone segment;
   the plate comprising a first, generally toroidal body at the first end of the plate, a second generally toroidal body at the second end of the plate, and a bridge connecting the first generally toroidal body to the second generally toroidal body;
   the first generally toroidal body comprising at least one opening extending therethrough and the second generally toroidal body comprising at least one opening extending therethrough;
   attachment apparatus adapted for positioning through the at least one opening in the first generally toroidal body for securing the first generally toroidal body to the first bone segment; and
   attachment apparatus adapted for positioning through the at least one opening in the second generally toroidal body for securing the second generally toroidal body to the second bone segment;
   wherein the attachment apparatus comprises a sleeve/screw construction, wherein the sleeve/screw construction comprises:
   a sleeve adapted for positioning through the at least one opening and into a bone segment, the sleeve comprising:
      a shank having a distal end and a proximal end and a recess extending from the distal end to the proximal end, wherein the recess narrows toward the distal end of the shank, and further wherein the distal end of the shank is slit so as to form a plurality of radially-expandable segments; and
      an enlarged head formed at the proximal end of the shank, the enlarged head being formed so as to be radially-expandable;
      the sleeve being sized so that when the sleeve is positioned through the at least one opening and into the bone segment, at least a portion of the radially-expandable segments extend into the bone segment; and
   a screw adapted for positioning in the recess in the sleeve, the screw being sized so as to (i) radially expand the distal end of the sleeve so that the sleeve is secured to the bone, and (ii) radially expand the enlarged head of the sleeve so that the sleeve is secured to the plate, whereby to secure the plate to the bone.

2. A surgical system according to claim 1 wherein the at least one opening has a non-circular configuration, and further wherein the enlarged head of the sleeve has a non-circular configuration, whereby to lock the sleeve against spinning within the plate when the screw is advanced into the recess of the sleeve.

3. A surgical system according to claim 1 wherein the enlarged head of the sleeve comprises a pair of diametrically-opposed, radially-projecting fingers extending outwardly from the enlarged head, and further wherein the at least one opening comprises a pair of diametrically-opposed, radially-extending depressions extending into the plate, the fingers and depressions mating with one another so as to form a pivot mount.

4. A surgical system according to claim 1 wherein the enlarged head of the sleeve comprises a pair of diametrically-opposed, radially-projecting fingers extending outwardly from the enlarged head, and further wherein the at least one opening comprises a pair of diametrically-opposed, radially-extending grooves extending into the plate, the fingers and grooves mating with one another so as to form a sliding mount.

5. A surgical system according to claim 1 wherein the plate further comprises at least one hole extending therethrough for receiving a pin extending therethrough for pinning the plate to bone.

6. A surgical system according to claim 1 wherein the system further comprises:
   a protective collar configured to be secured to the second generally toroidal body of the plate.

7. A surgical system according to claim 6 wherein the second generally toroidal body of the plate has an outer surface characterized by a plurality of locking surfaces, and further wherein the protective collar has an inner surface characterized by a plurality of corresponding locking surfaces, whereby to facilitate securing the protective collar to the second generally toroidal body of the plate.

8. A surgical system for stabilizing a first bone segment to a second bone segment, the system comprising:
   a plate having a first end and a second end, wherein the first end is configured to be secured to the first bone segment and the second end is configured to be secured to the second bone segment, and further wherein the plate has a structural integrity sufficient to stabilize the first bone segment to the second bone segment;

the plate comprising a first, generally toroidal body at the first end of the plate, a second generally toroidal body at the second end of the plate, and a bridge connecting the first generally toroidal body to the second generally toroidal body;

the first generally toroidal body comprising at least one opening extending therethrough for receiving attachment apparatus therethrough for securing the first generally toroidal body to the first bone segment, and the second generally toroidal body comprising at least one opening extending therethrough for receiving attachment apparatus therethrough for securing the second generally toroidal body to the second bone segment;

a supplemental plate for stabilizing a third bone segment to the second bone segment, the supplemental plate having a first end and a second end, wherein the first end is configured to be secured to the second generally toroidal body of the plate and the second end is configured to be secured to the third bone segment, and further wherein the supplemental plate has a structural integrity sufficient to stabilize the third bone segment to the second bone segment;

the supplemental plate comprising a first, generally toroidal body at the first end of the supplemental plate, a second generally toroidal body at the second end of the supplemental plate, and a bridge connecting the first generally toroidal body to the second generally toroidal body;

the first generally toroidal body comprising a cavity extending therethrough for mounting on the second generally toroidal body of the plate so as to secure the supplemental plate to the plate, and the second generally toroidal body comprising at least one opening extending therethrough for receiving attachment apparatus therethrough for securing the second generally toroidal body to the third bone segment.

9. A surgical system according to claim 8 wherein the attachment apparatus comprises a screw.

10. A surgical system according to claim 8 wherein the second generally toroidal body of the plate has an outer surface characterized by a taper, and further wherein the cavity of the first generally toroidal body of the supplemental plate has an inner surface characterized by a corresponding taper, whereby to facilitate mounting the first generally toroidal body of the supplemental plate to the second generally toroidal body of the plate.

11. A surgical system according to claim 8 wherein the second generally toroidal body of the plate has an outer surface characterized by a plurality of locking surfaces, and further wherein the cavity of the first generally toroidal body of the supplemental plate has an inner surface characterized by a plurality of corresponding locking surfaces, whereby to facilitate securing the first generally toroidal body of the supplemental plate to the second generally toroidal body of the plate.

12. A surgical system according to claim 11 wherein the locking surfaces comprise teeth.

13. A surgical system according to claim 11 wherein the locking surfaces comprise facets.

14. A surgical system according to claim 8 wherein the supplemental plate is mounted to the plate so that the supplemental plate is substantially axially aligned with the plate.

15. A surgical system according to claim 8 wherein the supplemental plate is mounted to the plate so that the supplemental plate extends at an angle to the plate.

16. A surgical system according to claim 8 wherein the first generally toroidal body of the supplemental plate comprises a strap for positioning over a portion of the plate, and further wherein the strap is secured to the plate.

17. A surgical system according to claim 8 wherein the bridge of the plate is cut back so as to provide an enhanced range of connections between the supplemental plate and the plate.

18. A surgical system according to claim 8 wherein the second generally toroidal body of the plate is cut back so as to provide an enhanced range of connections between the supplemental plate and the plate.

19. A surgical system according to claim 8 wherein the system further comprises:

a protective collar configured to be secured to the second generally toroidal body of the supplemental plate.

20. A surgical system according to claim 19 wherein the second generally toroidal body of the supplemental plate has an outer surface characterized by a plurality of locking surfaces, and further wherein the protective collar has an inner surface characterized by a plurality of corresponding locking surfaces, whereby to facilitate securing the protective collar to the second generally toroidal body of the supplemental plate.

21. A surgical system according to claim 8 wherein the system further comprises:

a second supplemental plate for stabilizing a fourth bone segment to the third bone segment, the second supplemental plate having a first end and a second end, wherein the first end is configured to be secured to the second generally toroidal body of the supplemental plate and the second end is configured to be secured to the fourth bone segment, and further wherein the second supplemental plate has a structural integrity sufficient to stabilize the fourth bone segment to the third bone segment;

the second supplemental plate comprising a first, generally toroidal body at the first end of the second supplemental plate, a second generally toroidal body at the second end of the second supplemental plate, and a bridge connecting the first generally toroidal body to the second generally toroidal body;

the first generally toroidal body comprising a cavity extending therethrough for mounting on the second generally toroidal body of the supplemental plate so as to secure the second supplemental plate to the supplemental plate, and the second generally toroidal body comprising at least one opening extending therethrough for receiving attachment apparatus therethrough for securing the second generally toroidal body to the fourth bone segment.

22. A method for stabilizing a first bone segment to a second bone segment and a third bone segment to the second bone segment, the method comprising:

providing a surgical system comprising:

a plate having a first end and a second end, wherein the first end is configured to be secured to the first bone segment and the second end is configured to be secured to the second bone segment, and further wherein the plate has a structural integrity sufficient to stabilize the first bone segment to the second bone segment;

the plate comprising a first, generally toroidal body at the first end of the plate, a second generally toroidal body at the second end of the plate, and a bridge connecting the first generally toroidal body to the second generally toroidal body;

the first generally toroidal body comprising at least one opening extending therethrough for receiving attachment apparatus therethrough for securing the first generally toroidal body to the first bone segment, and the second generally toroidal body comprising at least one opening extending therethrough for receiving attachment apparatus therethrough for securing the second generally toroidal body to the second bone segment;

a supplemental plate for stabilizing the third bone segment to the second bone segment, the supplemental plate having a first end and a second end, wherein the first end is configured to be secured to the second generally toroidal body of the plate and the second end is configured to be secured to the third bone segment, and further wherein the supplemental plate has a structural integrity sufficient to stabilize the third bone segment to the second bone segment;

the supplemental plate comprising a first, generally toroidal body at the first end of the supplemental plate, a second generally toroidal body at the second end of the supplemental plate, and a bridge connecting the first generally toroidal body to the second generally toroidal body;

the first generally toroidal body comprising a cavity extending therethrough for mounting on the second generally toroidal body of the plate so as to secure the supplemental plate to the plate, and the second generally toroidal body comprising at least one opening extending therethrough for receiving attachment apparatus therethrough for securing the second generally toroidal body to the third bone segment;

securing the first generally toroidal body to the first bone segment and securing the second generally toroidal body to the second bone segment so as to stabilize the first bone segment to the second bone segment; and securing the first generally toroidal body of the supplemental plate to the plate and securing the second generally toroidal body of the supplemental plate to the third bone segment so as to stabilize the third bone segment to the second bone segment.

* * * * *